United States Patent [19]

Huston et al.

[11] Patent Number: 5,753,204
[45] Date of Patent: May 19, 1998

[54] BIOSYNTHETIC BINDING PROTEINS FOR IMMUNOTARGETING

[75] Inventors: James S. Huston, Chestnut Hill, Mass.; L. L. Houston, Oakland; David B. Ring, Redwood City, both of Calif.; Hermann Oppermann, Medway, Mass.

[73] Assignees: Chiron Corporation, Emeryville, Calif.; Creative BioMolecules, Inc., Hopkinton, Mass.

[21] Appl. No.: 461,838

[22] Filed: Jun. 5, 1995

Related U.S. Application Data

[60] Division of Ser. No. 133,804, Oct. 7, 1993, Pat. No. 5,534,254, which is a continuation-in-part of Ser. No. 831,967, Feb. 6, 1992, abandoned.

[51] Int. Cl.⁶ .......................... A61K 49/00; A61K 51/00; A61K 39/395
[52] U.S. Cl. .................. 424/1.49; 424/1.53; 424/130.1; 424/132.1; 424/135.1; 424/138.1; 424/9.3; 435/696; 435/172.1; 435/172.3; 435/240.27; 435/252.23; 530/387.3
[58] Field of Search .................. 424/130.1, 132.1, 424/135.1, 138.1, 1.49, 1.53, 9.3; 435/69.6, 172.1, 172.3, 240.27, 252.23; 530/387.3

[56] References Cited

U.S. PATENT DOCUMENTS

| 4,472,509 | 9/1984 | Gansow et al. | 436/548 |
|---|---|---|---|
| 4,479,930 | 10/1984 | Hnatowich | 424/1.1 |
| 4,753,894 | 6/1988 | Frankel et al. | 436/548 |
| 4,946,778 | 8/1990 | Ladner et al. | 435/69.6 |
| 5,091,513 | 2/1992 | Huston et al. | 530/387 |
| 5,132,405 | 7/1992 | Huston et al. | 530/387.3 |
| 5,258,498 | 11/1993 | Huston et al. | 530/350 |
| 5,260,203 | 11/1993 | Ladner et al. | 435/172.3 |
| 5,571,894 | 11/1996 | Wels et al. | |
| 5,587,458 | 12/1996 | King et al. | |

FOREIGN PATENT DOCUMENTS

| 0502812 A1 | 9/1992 | European Pat. Off. |
|---|---|---|
| WO85/03523 | 8/1985 | WIPO |
| WO88/09344 | 1/1988 | WIPO |
| WO92/15682 | 9/1992 | WIPO |
| WO93/06217 | 4/1993 | WIPO |
| WO93/11161 | 6/1993 | WIPO |
| WO93/11162 | 6/1993 | WIPO |
| WO93/15210 | 8/1993 | WIPO |

OTHER PUBLICATIONS

Houston, Abstract from NIH Grant, Serial No. U01 CA51880–05.
Plückthum (1992) "Mono–and Bivalent Antibody Fragments Produced in *Escherichia coli*: Engineering, Folding and Antigen Binding," *Immunological Reviews*, 130:151–188.
Saul et al. (1978) The Journal of Biological Chemistry, vol. 253, No. 2, pp. 585–597, "Preliminary Refinement and Structural Analysis of the Fab Fragment from Human Immunoglobulin New at 2.0 A Resolution".

Khaw et al. (1980) Science, vol. 209, No. 4453, pp. 295–297, "Myocardial Infarct Imaging of Antibodies to Canine Cardiac Myosin with Indium–111–Diethylenetriamine Pentaacetic Acid".
Kunkel (1985) Proc. Natl. Acad. Sci. vol. 82, pp. 488–492, "Rapid and efficient site–specific mutagenesis without phenotypic selection".
Chen et al. (1985) DNA, vol. 4, No. 2, pp. 165–170, "Laboratory Methods Supercoil Sequencing: A Fast and Simple Method for Sequencing Plasmid DNA".
Bjorn et al. (1985) Cancer Research, vol. 45, pp. 1214–1221, "Evaluation of Monocolonal Antibodies for the Development of Breast Cancer Immunotoxins".
Fisher et al. (1986) Journal of Clinical Oncology, vol. 4, No. 6, pp. 929–941, "Ten–Year Results From the National Surgical Adjuvant Breast and Bowel Project (NSABP) Clinical Trial Evaluating the Use of L–Phenylalanine Mustard (L–PAM) in the Management of Primary Breast Cancer".
Satow et al. (1986) J. Mol. Biol., vol. 190, pp. 593–604, "Phosphocholine Binding Immunoglubolin Fab McPC603 An X–ray Diffraction Study at 2.7 A".
Amit et al. (1986) Science, vol. 233, pp. 747–753, "Three–Dimensional Structure of An Antigen–Antibody Complex at 2.8 A Resolution".
Sheriff et al. (1987) Proc. Natl. Acad. Sci. USA, vol. 84, pp. 8075–8079, "Three–dimensional structure of an antibody–antigen complex".
Colman et al. (1987) Nature, vol. 326, pp. 358–363, "Three–dimensional structure of a complex of antibody with influenza virus neuraminidase".
Bartlet et al. (1987) The Lancet, vol. II, No. 8552, pp. 171–175, "Adjuvant Tamoxifen in the Management of Operable Breast Cancer: The Scottish Trial".
Aisner et al. (1987) Journal of Clincical Oncology, vol. 5, No. 10, pp. 1523–1533, "Chemotherapy Versus Chemoimmunotherapy (CAF v CAFVP v CMF Each±MER) for Metastatic Carcinoma of the Breast : A CALGB Study".
Huston et al. (1988) Proc. Natl. Acad. Sci., Vo. 85, pp. 5879–5883, "Protein engineering of antibody binding sites: Recovery of specific activity in an anti–digoxin single–chain Fv analogue produced in *Eschericha coli*".
Sefton (1988) Trends in Genetics, vol. 4, No. 9, pp. 247–248, "neus about c–erb–B–2 and HER2".

(List continued on next page.)

*Primary Examiner*—Frank C. Eisenschenk
*Attorney, Agent, or Firm*—Testa Hurwitz & Thibeault, LLP

[57] ABSTRACT

Disclosed is a formulation for targeting an epitope on an antigen expressed in a mammal. The formulation comprises a pharmaceutically acceptable carrier together with a dimeric biosynthetic construct for binding at least one preselected antigen. The biosynthetic construct contains two polypeptide chains, each of which define single-chain Fv (sFv) binding proteins and have C-terminal tails that facilitate the crosslinking of two sFv polypeptides. The resulting dimeric constructs have a conformation permitting binding of a preselected antigen by the binding site of each polypeptide chain when administered to a mammal. The formulation has particular utility in in vivo imaging and drug targeting experiments.

21 Claims, 6 Drawing Sheets

OTHER PUBLICATIONS

Bird, et al. (1988) Science, vol. 242, pp. 423–426, "Single–Chain Antigen–Binding Proteins".

Vogel et al. (1988) Biochemistry, vol. 28, pp. 2961–2966, "Binding Domains and Epitopes in Platelet–Derived Growth Factor".

Orlandi et al. (1989) Proc. Natl. Acad. Sci. USA, vol. 86, pp. 3833–3837, "Cloning immunoglobulin variable domains for expression by the polymerase chain reaction".

Ring et al. (1989) Cancer Research vol. 49, No. 11, pp. 3070–3080, "Distribution and Physical Properties of BCA200, a $M_r$200,000 Glycoprotein Selectively Associated with Human Breast Cancer".

Dillman (1989), Annals of Internal Medicine, vol. 111, pp. 592–603, "Monoclonal Antibodies for Treating Cancer".

Glockshuber et al. (1990) Biochemistry, vol. 29, pp. 1362–1367, "A Comparison of Strategies to Stabilize Immunoglobulin $F_v$-Fragments".

Queen et al. (1989) Proc. Natl. acad. Sci., vol. 86, pp. 10029–10033, "A humanized antibody that binds to the interleukin 2 receptor".

Hird et al. (1990) Genes and Cancer, pp. 183–189, "Immunotherapy with Monoclonal Antibodies".

Batra et al. (1990) The Journal of Biological Chemistry, vol. 265, No. 25, pp. 15198–15202, "Anti–Tac(Fv)–PE40, a Single Chain Antibody Pseudomonas Fusion Protein Directed at Interleukin 2 Receptor Bearing Cells".

McGuire et al. (1990) Journal of the National Cancer Institute, vol. 82, No. 12, pp. 1006–1015, "How to Use Prognostic Factors in Axillary Node–Negative Breast Cancer Patients".

Shealy et al. (1990) The Journal of Nuclear Medicine, vol. 31, No. 5, Abstract Book Proceedings of the 37th Annual Meeting, "Characteriza–Characterization and Biodistribution of Tc–99m Labled Single Chain Antibody Fv Fragment (sFv)".

Colcher et al. (1990) J. Natl. Cancer Inst., vol. 82, No. 14, pp. 1192–1197, "In Vivo Tumor Targeting of a Recombinant Single–Chain Antigen–Binding Protein".

Batra et al. (1990) Biochemical and Biophysical Research Communications vol. 171, No. 1, pp. 1–6, "TGFa–anti–Tac(Fv)–PE40: A Bifunctional Toxin Cytotoxic for Cells with EGF or IL2 Receptors".

Tai et al. (1990) Biochemistry, vol. 29, pp. 8024–8030, "A Bifunctional Fusion Protein Containing Fc–Binding Fragment of B of Staphylococcal Protein A Amino terminal to Antidigoxin Single–Chain Fv".

Huston et al. (1990) Bispecific Antibodies and Targeted Cellular Cytotoxicity, Second International Conference, pp. 201–206, "Bifunctional Single–Chain Fv Fusion Proteins".

Huston et al. (1990) Academic Press, Inc., Methods in Enzymology, vol. 203, pp. 46–89, "Protein Engineering of Single–Chain Fv Analogs and Fusion Proteins".

Whitlow et al. (1991), Methods: A Companion to Methods in Enzymology, vol. 2, No. 2, pp. 97–105, "Single–Chain Fv Proteins and Their Fusion Proteins".

Nedelman et al. (1991) Abstract Form for Scientific Papers, No. 32070 The Society of Nuclear Medicine 38th Annual Meeting, "Rapid Infarct Imaging with a New Tc–99m Antimyosin sFv Fragment: Evaluation in Acute Myocardial Infarction in Dogs".

Waldmann (1991) Science, vol. 252, pp. 1657–1662, "Monoclonal Antibodies in Diagnosis and Therapy".

Clackson et al. (1991) Nature, vol. 352, pp. 624–628, "Making antibody fragments using phage display libraries".

Ring et al. (1991) Molecular Immunology, vol. 28, No. 8, pp. 915–917, "Identity of BCA200 and c–erbB–2 Indicated by Reactivity of Monoclonal Antibodies with Recombinant c–erbB–2".

Milenic et al. (1991) Cancer Research, vol. 51, pp. 6363–6371, "Construction, Binding Properties, Metabolism, and Tumopr Targeting of a Single–Chain Fv Derived from the Pancarcinoma Monoclonal Antibody CC49".

Wels et al. (1992) J. Steroid Biochem. Molec. Biol., vol. 43, No. 1–3, pp 1–7, "Diminution of Antibodies Directed Against Tumor Cell Surface Epitopes: A Single Chain Fv Fusion Molecule Specifically Recognizes the Extracellular Domain of the c–erbB–2 Receptor".

Pack et al. (1992) Biochemistry, vol. 31, No. 6, pp. 1579–1584, "Miniantibodies: Use of Amphipathic Helics to Produce Functional, Flexibility Linked Dimeric Fv Fragments with High Avidity in *Escherichia coli*".

Yokota et al. (1992) Cancer Research, vol. 52, pp. 3402–3408, "Rapid Tumor Penetration of a Single–Chain Fv and Comparision with Other Immunoglobulin Forms".

Cumber et al. (1992) The Journal of Immunology, vol. 149, No. 1, pp. 120–126, "Comparative Stabilities in Vitro and Vivo of a Recombinant Mouse Antibody FvCys Fragment and a bisFvCys Conjugate".

Wels et al. (1992) Biotechnology, vol. 10, pp. 1128–1132, "Construction, Bacterial Expression and Characterization of a Bifunctional Single–Chain Antibody–Phosphatase Fusion Protein Targeted to the Human ERBB–2 Receptor".

Schott et al. (1992) Cancer Research, vol. 52, pp. 6413–6417, "Differential Metabolic Patterns of Iodinated versus Radiometal Chelated Anticarcinoma Single–Chain Fv Molecules".

Wels et al. (1992) Cancer Research, vol. 52, pp. 6310–6317, "Selective Inhibition of Tumor Cell Growth by a Recombinant Single–Chain Antibody Toxin Specific for the erbB–2 Receptor".

Nedelman et al. (1993) The Journal of Nuclear Medicine, vol. 34, pp. 234–241, "Rapid Infarct Imaging with a Technitium–99m–Labeled Antimyosin Recombinant Single–Chain Fv: Evaluation in a Canine Model of Acute Myocoardial Infarction".

Adams et al. (1993) Abstract, International Conference on Monoclonal Antibody Immunoconjugates for Cancer, "Demonstration of in vivo specificity of 125I–741F8 sFv, a single–chain Fv molecule".

Huston et al. (1993) Immunotechnology, Proceedings of the 21st Federal of European Biochemical Societies Meeting, Dublin, pp. 47–60, "Single–chain immunotechnology of Fv analogues and fusion proteins".

McCartney et al. (1993) Biotechnology, Advances in Gene Technology Protein Engineering and Beyond, Proceedings of the 1993 Miami Bio/Technology Winter Symposium, "Refolding of Single–Chain Fv with c–Terminal Cysteine (sFv'): Formation of Disulfide–Bonded Homodimers of Anti–c–erbB–2 and Anti–digoxin sFv'".

Huston et al. (1993) Intern. Rev. Immunol., vol. 10, pp. 195–217, "Medical Applications of Single–Chain Antibodies".

Adams et al. (May 1993) Abstract, The Tenth International Hammersmith Conference, "Demonstration of in vivo tumor specificity of monovalent and divalent forms of 125I–741F8 sFv, an anti–c–erbB–2 single–chain Fv molecule".

Huston et al. (May 1993) Abstract for the 10th Hammersmith Meeting "Refolding and Characterization of single-chain Fv analogues having C-terminal cysteine (sFv): physicochemical behavior in vitro and tumor localization in vivo of monovalent sFv and bivalent (sFv)$_2$ species directed to the c–erbB–2 tumor antigen and digoxin".

Holliger et al. (1993) Proc. Natl. Acad. Sci. USA, vol. 90, pp. 6444–6448, "Diabodies: Small bivalent and bispecific antibody fragments".

Adams et al. (1993) Cancer Research, vol. 53, pp. 4026–4034, "Highly Specific in Vivo Targeting by Monovalent and Divalent Forms of 741F8 Anti–c–erbB–2 Single–Chain Fv[1]".

Jacobs (1991) Biotechnology 9: 258–262.

Reichmann et al. (1988) Nature 332: 323–327.

TUMOR: ORGAN RATIOS OF sFv' and (sFv')₂ SPECIES

| ORGAN | 741F8 sFv' | 741F8 (sFv')₂ | 741F8 (Gly₄Cys-sFv')₂ | 741F8 MCA-(sFv')₂ | 26-10 (sFv')₂ |
|---|---|---|---|---|---|
| TUMOR | 1.0 | 1.0 | 1.0 | 1.0 | 1.0 |
| LIVER | 9.2 | 5.9 | 10.0 | 21.2 | 2.2 |
| SPLEEN | 13.4* | 0.9 | 6.2 | 16.4 | 1.8 |
| KIDNEY | 1.6* | 2.3 | 3.0 | 6.6 | 0.5 |
| LUNG | 4.9* | 0.6 | 6.4 | 9.3 | 1.4 |
| MUSCLE | 51.2* | 100.0 | 74.6 | 92.9 | 15.0* |
| HEART | 16.5 | 20.0 | 19.0 | 32.6 | 4.4 |
| STOMACH | 2.7* | 11.1 | 11.5 | 13.5 | 1.6* |
| INTESTINE | 20.4* | 25.0 | 30.7 | 26.5 | 5.3 |

*SEM< 40% OF DEPICTED VALUE

Fig. 4

PERCENTAGE OF INJECTED DOSE PER GRAM OF TUMOR FOR sFv' AND (sFv')₂ SPECIES

| ORGAN | 741F8 sFv' | 741F8 (sFv')₂ | 741F8 (Gly₄Cys-sFv')₂ | 741F8 MCA-(sFv')₂ | 26-10 (sFv')₂ |
|---|---|---|---|---|---|
| TUMOR | 1.00 | 1.00* | 1.60 | 1.86 | 0.22 |
| LIVER | 0.11 | 0.17 | 0.16 | 0.09 | 0.11 |
| SPLEEN | 0.10 | 1.05 | 0.26 | 0.12 | 0.13 |
| KIDNEY | 0.64 | 0.43 | 0.55 | 0.28 | 0.45 |
| LUNG | 0.73 | 1.61* | 0.26 | 0.22 | 0.18 |
| MUSCLE | 0.02 | 0.01 | 0.02 | 0.02 | 0.02 |
| HEART | 0.07 | 0.05 | 0.08 | 0.06 | 0.06 |
| STOMACH | 0.49 | 0.09 | 0.17 | 0.15 | 0.22 |
| INTESTINE | 0.06 | 0.04 | 0.06 | 0.07 | 0.05 |

*SEM< 40% OF DEPICTED VALUE

Fig. 5

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 909 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..752
        ( D ) OTHER INFORMATION: /product="741F8 sFv'C-terminal Gly4-Cys"

( x i ) SEQUENCE DESCRIPTION: SEQ ID NO:1:

```
CC ATG GCG GAG ATC CAA TTG GTG CAG TCT GGA CCT GAG CTG AAG AAG            47
   Met Ala Glu Ile Gln Leu Val Gln Ser Gly Pro Glu Leu Lys Lys
   1               5                   10                  15

CCT GGA GAG ACA GTC AAG ATC TCC TGC AAG GCT TCT GGG TAT ACC TTC           95
Pro Gly Glu Thr Val Lys Ile Ser Cys Lys Ala Ser Gly Tyr Thr Phe
                20                  25                  30

ACA AAC TAT GGA ATG AAC TGG GTG AAG CAG GCT CCA GGA AAG GGT TTA          143
Thr Asn Tyr Gly Met Asn Trp Val Lys Gln Ala Pro Gly Lys Gly Leu
            35                  40                  45

AAG TGG ATG GGC TGG ATA AAC ACC AAC ACT GGA GAG CCA ACA TAT GCT          191
Lys Trp Met Gly Trp Ile Asn Thr Asn Thr Gly Glu Pro Thr Tyr Ala
        50                  55                  60

GAA GAG TTC AAG GGA CGG TTT GCC TTC TCT TTG GAA ACC TCT GCC AGC          239
Glu Glu Phe Lys Gly Arg Phe Ala Phe Ser Leu Glu Thr Ser Ala Ser
    65                  70                  75
```

-continued

| | | | | | | | | | | | | | | | | |
|---|---|---|---|---|---|---|---|---|---|---|---|---|---|---|---|---|
|ACT|GCC|TAT|TTG|CAG|ATC|AAC|AAC|CTC|AAA|AAT|GAG|GAC|ACG|GCT|ACA|287|
|Thr|Ala|Tyr|Leu|Gln|Ile|Asn|Asn|Leu|Lys|Asn|Glu|Asp|Thr|Ala|Thr| |
|80| | | | |85| | | |90| | | | |95| | |

| | | | | | | | | | | | | | | | | |
|---|---|---|---|---|---|---|---|---|---|---|---|---|---|---|---|---|
|TAT|TTC|TGT|GGA|AGG|CAA|TTT|ATT|ACC|TAC|GGC|GGG|TTT|GCT|AAC|TGG|335|
|Tyr|Phe|Cys|Gly|Arg|Gln|Phe|Ile|Thr|Tyr|Gly|Gly|Phe|Ala|Asn|Trp| |
| | | | |100| | | | |105| | | | |110| | |

| | | | | | | | | | | | | | | | | |
|---|---|---|---|---|---|---|---|---|---|---|---|---|---|---|---|---|
|GGC|CAA|GGG|ACT|CTG|GTC|ACT|GTC|TCT|GCA|TCG|AGC|TCC|TCC|GGA|TCT|383|
|Gly|Gln|Gly|Thr|Leu|Val|Thr|Val|Ser|Ala|Ser|Ser|Ser|Ser|Gly|Ser| |
| | | |115| | | | |120| | | | |125| | | |

| | | | | | | | | | | | | | | | | |
|---|---|---|---|---|---|---|---|---|---|---|---|---|---|---|---|---|
|TCA|TCT|AGC|GGT|TCC|AGC|TCG|AGC|GAT|ATC|GTC|ATG|ACC|CAG|TCT|CCT|431|
|Ser|Ser|Ser|Gly|Ser|Ser|Ser|Ser|Asp|Ile|Val|Met|Thr|Gln|Ser|Pro| |
| | |130| | | | |135| | | | |140| | | | |

| | | | | | | | | | | | | | | | | |
|---|---|---|---|---|---|---|---|---|---|---|---|---|---|---|---|---|
|AAA|TTC|ATG|TCC|ACG|TCA|GTG|GGA|GAC|AGG|GTC|AGC|ATC|TCC|TGC|AAG|479|
|Lys|Phe|Met|Ser|Thr|Ser|Val|Gly|Asp|Arg|Val|Ser|Ile|Ser|Cys|Lys| |
| |145| | | | |150| | | | |155| | | | | |

| | | | | | | | | | | | | | | | | |
|---|---|---|---|---|---|---|---|---|---|---|---|---|---|---|---|---|
|GCC|AGT|CAG|GAT|GTG|AGT|ACT|GCT|GTA|GCC|TGG|TAT|CAA|CAA|AAA|CCA|527|
|Ala|Ser|Gln|Asp|Val|Ser|Thr|Ala|Val|Ala|Trp|Tyr|Gln|Gln|Lys|Pro| |
|160| | | | |165| | | | |170| | | | |175| |

| | | | | | | | | | | | | | | | | |
|---|---|---|---|---|---|---|---|---|---|---|---|---|---|---|---|---|
|GGG|CAA|TCT|CCT|AAA|CTA|CTG|ATT|TAC|TGG|ACA|TCC|ACC|CGG|CAC|ACT|575|
|Gly|Gln|Ser|Pro|Lys|Leu|Leu|Ile|Tyr|Trp|Thr|Ser|Thr|Arg|His|Thr| |
| | | | |180| | | | |185| | | | |190| | |

| | | | | | | | | | | | | | | | | |
|---|---|---|---|---|---|---|---|---|---|---|---|---|---|---|---|---|
|GGA|GTC|CCT|GAT|CGC|TTC|ACA|GGC|AGT|GGA|TCT|GGG|ACA|GAT|TAT|ACT|623|
|Gly|Val|Pro|Asp|Arg|Phe|Thr|Gly|Ser|Gly|Ser|Gly|Thr|Asp|Tyr|Thr| |
| | | |195| | | | |200| | | | |205| | | |

| | | | | | | | | | | | | | | | | |
|---|---|---|---|---|---|---|---|---|---|---|---|---|---|---|---|---|
|CTC|ACC|ATC|AGC|AGT|GTG|CAG|GCT|GAA|GAC|CTG|GCA|CTT|CAT|TAC|TGT|671|
|Leu|Thr|Ile|Ser|Ser|Val|Gln|Ala|Glu|Asp|Leu|Ala|Leu|His|Tyr|Cys| |
| | |210| | | | |215| | | | |220| | | | |

| | | | | | | | | | | | | | | | | |
|---|---|---|---|---|---|---|---|---|---|---|---|---|---|---|---|---|
|CAG|CAA|CAT|TAT|AGA|GTG|CCG|TAC|ACG|TTC|GGA|GGG|GGG|ACC|AAG|CTG|719|
|Gln|Gln|His|Tyr|Arg|Val|Pro|Tyr|Thr|Phe|Gly|Gly|Gly|Thr|Lys|Leu| |
| |225| | | | |230| | | | |235| | | | | |

| | | | | | | | | | | | | |
|---|---|---|---|---|---|---|---|---|---|---|---|---|
|GAG|ATA|AAA|CGG|GCT|GAT|GGG|GGA|GGT|GGA|TGT|TAACGGGGGA|GGTGGATGTT|772|
|Glu|Ile|Lys|Arg|Ala|Asp|Gly|Gly|Gly|Gly|Cys| | | |
|240| | | | |245| | | | |250| | | |

| | | | |
|---|---|---|---|
|GGGTCTCGTT|ACGTTGCGGA|TCTCGAGGCT|ATCTTTACTA|ACTCTTACCG|TAAAGTTCTG|832|
|GCTCAACTGT|CTGCACGCAA|GCTTTTGCAG|GATATCATGA|GCGCTTAAGA|TCCGTCGACC|892|
|TGCAGGCATG|CAAGCTT| | | | |909|

( 2 ) INFORMATION FOR SEQ ID NO:2:

( i ) SEQUENCE CHARACTERISTICS:
        ( A ) LENGTH: 250 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
|Met|Ala|Glu|Ile|Gln|Leu|Val|Gln|Ser|Gly|Pro|Glu|Leu|Lys|Lys|Pro|
|1| | | |5| | | | |10| | | | |15| |

| | | | | | | | | | | | | | | | |
|---|---|---|---|---|---|---|---|---|---|---|---|---|---|---|---|
|Gly|Glu|Thr|Val|Lys|Ile|Ser|Cys|Lys|Ala|Ser|Gly|Tyr|Thr|Phe|Thr|
| | | |20| | | | |25| | | | |30| | |

| | | | | | | | | | | | | | |
|---|---|---|---|---|---|---|---|---|---|---|---|---|---|
|Asn|Tyr|Gly|Met|Asn|Trp|Val|Lys|Gln|Ala|Pro|Gly|Lys|Gly|Leu|Lys|
| | |35| | | | |40| | | | |45| | | |

| | | | | | | | | | | | | | | | |
|---|---|---|---|---|---|---|---|---|---|---|---|---|---|---|---|
|Trp|Met|Gly|Trp|Ile|Asn|Thr|Asn|Thr|Gly|Glu|Pro|Thr|Tyr|Ala|Glu|
| |50| | | | |55| | | | |60| | | | |

| | | | | | | | | | | | | | | | |
|---|---|---|---|---|---|---|---|---|---|---|---|---|---|---|---|
|Glu|Phe|Lys|Gly|Arg|Phe|Ala|Phe|Ser|Leu|Glu|Thr|Ser|Ala|Ser|Thr|
|65| | | | |70| | | | |75| | | | |80|

| | | | | | | | | | | | | | | | |
|---|---|---|---|---|---|---|---|---|---|---|---|---|---|---|---|
|Ala|Tyr|Leu|Gln|Ile|Asn|Asn|Leu|Lys|Asn|Glu|Asp|Thr|Ala|Thr|Tyr|
| | | | |85| | | | |90| | | | |95| |

| | | | | | | | | | | | | | | |
|---|---|---|---|---|---|---|---|---|---|---|---|---|---|---|
| Phe | Cys | Gly | Arg<br>100 | Gln | Phe | Ile | Thr | Tyr<br>105 | Gly | Gly | Phe | Ala | Asn<br>110 | Trp | Gly |
| Gln | Gly | Thr<br>115 | Leu | Val | Thr | Val | Ser<br>120 | Ala | Ser | Ser | Ser<br>125 | Gly | Ser | Ser |
| Ser | Ser<br>130 | Gly | Ser | Ser | Ser | Ser<br>135 | Asp | Ile | Val | Met | Thr<br>140 | Gln | Ser | Pro | Lys |
| Phe<br>145 | Met | Ser | Thr | Ser | Val<br>150 | Gly | Asp | Arg | Val | Ser<br>155 | Ile | Ser | Cys | Lys | Ala<br>160 |
| Ser | Gln | Asp | Val | Ser<br>165 | Thr | Ala | Val | Ala | Trp<br>170 | Tyr | Gln | Gln | Lys | Pro<br>175 | Gly |
| Gln | Ser | Pro | Lys<br>180 | Leu | Leu | Ile | Tyr | Trp<br>185 | Thr | Ser | Thr | Arg | His<br>190 | Thr | Gly |
| Val | Pro | Asp<br>195 | Arg | Phe | Thr | Gly | Ser<br>200 | Gly | Ser | Gly | Thr | Asp<br>205 | Tyr | Thr | Leu |
| Thr | Ile<br>210 | Ser | Ser | Val | Gln | Ala<br>215 | Glu | Asp | Leu | Ala | Leu<br>220 | His | Tyr | Cys | Gln |
| Gln<br>225 | His | Tyr | Arg | Val | Pro<br>230 | Tyr | Thr | Phe | Gly | Gly<br>235 | Gly | Thr | Lys | Leu | Glu<br>240 |
| Ile | Lys | Arg | Ala | Asp<br>245 | Gly | Gly | Gly | Gly | Cys<br>250 | | | | | | |

( 2 ) INFORMATION FOR SEQ ID NO:3:

( i ) SEQUENCE CHARACTERISTICS:
        ( A ) LENGTH: 779 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..758
        ( D ) OTHER INFORMATION: /product="26-10 sFv' with
            C-terminal Gly4-Cys"

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| CC | ATG<br>Met<br>1 | GAA<br>Glu | GTT<br>Val | CAA<br>Gln | CTG<br>Leu<br>5 | CAA<br>Gln | CAG<br>Gln | TCT<br>Ser | GGT<br>Gly | CCT<br>Pro<br>10 | GAA<br>Glu | TTG<br>Leu | GTT<br>Val | AAA<br>Lys | CCT<br>Pro<br>15 | 47 |
| GGC<br>Gly | GCC<br>Ala | TCT<br>Ser | GTG<br>Val | CGC<br>Arg<br>20 | ATG<br>Met | TCC<br>Ser | TGC<br>Cys | AAA<br>Lys | TCC<br>Ser<br>25 | TCT<br>Ser | GGG<br>Gly | TAC<br>Tyr | ATT<br>Ile | TTC<br>Phe | ACC<br>Thr<br>30 | 95 |
| GAC<br>Asp | TTC<br>Phe | TAC<br>Tyr | ATG<br>Met | AAT<br>Asn<br>35 | TGG<br>Trp | GTT<br>Val | CGC<br>Arg | CAG<br>Gln | TCT<br>Ser<br>40 | CAT<br>His | GGT<br>Gly | AAG<br>Lys | TCT<br>Ser | CTA<br>Leu<br>45 | GAC<br>Asp | 143 |
| TAC<br>Tyr | ATC<br>Ile | GGG<br>Gly<br>50 | TAC<br>Tyr | ATT<br>Ile | TCC<br>Ser | CCA<br>Pro | TAC<br>Tyr<br>55 | TCT<br>Ser | GGG<br>Gly | GTT<br>Val | ACC<br>Thr | GGC<br>Gly<br>60 | TAC<br>Tyr | AAC<br>Asn | CAG<br>Gln | 191 |
| AAG<br>Lys | TTT<br>Phe<br>65 | AAA<br>Lys | GGT<br>Gly | AAG<br>Lys | GCG<br>Ala | ACC<br>Thr<br>70 | CTT<br>Leu | ACT<br>Thr | GTC<br>Val | GAC<br>Asp | AAA<br>Lys<br>75 | TCT<br>Ser | TCC<br>Ser | TCA<br>Ser | ACT<br>Thr | 239 |
| GCT<br>Ala<br>80 | TAC<br>Tyr | ATG<br>Met | GAG<br>Glu | CTG<br>Leu | CGT<br>Arg<br>85 | TCT<br>Ser | TTG<br>Leu | ACC<br>Thr | TCT<br>Ser | GAG<br>Glu<br>90 | GAC<br>Asp | TCC<br>Ser | GCG<br>Ala | GTA<br>Val | TAC<br>Tyr<br>95 | 287 |
| TAT<br>Tyr | TGC<br>Cys | GCG<br>Ala | GGC<br>Gly | TCC<br>Ser<br>100 | TCT<br>Ser | GGT<br>Gly | AAC<br>Asn | AAA<br>Lys | TGG<br>Trp<br>105 | GCC<br>Ala | ATG<br>Met | GAT<br>Asp | TAT<br>Tyr | TGG<br>Trp<br>110 | GGt<br>Gly | 335 |
| CAT<br>His | GGT<br>Gly | GCT<br>Ala | AGC<br>Ser | GTT<br>Val<br>115 | ACT<br>Thr | GTG<br>Val | AGC<br>Ser | TCC<br>Ser | TCC<br>Ser<br>120 | GGA<br>Gly | TCT<br>Ser | TCA<br>Ser | TCT<br>Ser | AGC<br>Ser<br>125 | GGT<br>Gly | 383 |

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| TCC | AGC | TCG | AGT | GGA | TCC | GAC | GTC | GTA | ATG | ACC | CAG | ACT | CCG | CTG | TCT | 431 |
| Ser | Ser | Ser | Ser | Gly | Ser | Asp | Val | Val | Met | Thr | Gln | Thr | Pro | Leu | Ser |     |
|     |     | 130 |     |     |     |     | 135 |     |     |     |     | 140 |     |     |     |     |
| CTG | CCG | GTT | TCT | CTG | GGT | GAC | CAG | GCT | TCT | ATT | TCT | TGC | CGC | TCT | TCC | 479 |
| Leu | Pro | Val | Ser | Leu | Gly | Asp | Gln | Ala | Ser | Ile | Ser | Cys | Arg | Ser | Ser |     |
|     | 145 |     |     |     |     | 150 |     |     |     |     | 155 |     |     |     |     |     |
| CAG | TCT | CTG | GTC | CAT | TCT | AAT | GGT | AAC | ACT | TAC | CTG | AAC | TGG | TAC | CTG | 527 |
| Gln | Ser | Leu | Val | His | Ser | Asn | Gly | Asn | Thr | Tyr | Leu | Asn | Trp | Tyr | Leu |     |
| 160 |     |     |     |     | 165 |     |     |     |     | 170 |     |     |     |     | 175 |     |
| CAA | AAG | GCT | GGT | CAG | TCT | CCG | AAG | CTT | CTG | ATC | TAC | AAA | GTC | TCT | AAC | 575 |
| Gln | Lys | Ala | Gly | Gln | Ser | Pro | Lys | Leu | Leu | Ile | Tyr | Lys | Val | Ser | Asn |     |
|     |     |     |     | 180 |     |     |     |     | 185 |     |     |     |     | 190 |     |     |
| CGC | TTC | TCT | GGT | GTC | CCG | GAT | CGT | TTC | TCT | GGT | TCT | GGT | TCT | GGT | ACT | 623 |
| Arg | Phe | Ser | Gly | Val | Pro | Asp | Arg | Phe | Ser | Gly | Ser | Gly | Ser | Gly | Thr |     |
|     |     |     | 195 |     |     |     |     | 200 |     |     |     |     | 205 |     |     |     |
| GAC | TTC | ACC | CTG | AAG | ATC | TCT | CGT | GTC | GAG | GCC | GAA | GAC | CTG | GGT | ATC | 671 |
| Asp | Phe | Thr | Leu | Lys | Ile | Ser | Arg | Val | Glu | Ala | Glu | Asp | Leu | Gly | Ile |     |
|     |     | 210 |     |     |     |     | 215 |     |     |     |     | 220 |     |     |     |     |
| TAC | TTC | TGC | TCT | CAG | ACT | ACT | CAT | GTA | CCG | CCG | ACT | TTT | GGT | GGT | GGC | 719 |
| Tyr | Phe | Cys | Ser | Gln | Thr | Thr | His | Val | Pro | Pro | Thr | Phe | Gly | Gly | Gly |     |
|     |     | 225 |     |     |     |     | 230 |     |     |     |     | 235 |     |     |     |     |
| ACC | AAG | CTC | GAG | ATT | AAA | CGT | TCC | GGG | GGA | GGT | GGA | TGT | TAACTGCAGC |  |  | 768 |
| Thr | Lys | Leu | Glu | Ile | Lys | Arg | Ser | Gly | Gly | Gly | Gly | Cys |     |     |     |     |
| 240 |     |     |     |     | 245 |     |     |     |     | 250 |     |     |     |     |     |     |
| CCGGGGATC | C |     |     |     |     |     |     |     |     |     |     |     |     |     |     | 779 |

( 2 ) INFORMATION FOR SEQ ID NO:4:

( i ) SEQUENCE CHARACTERISTICS:
        ( A ) LENGTH: 252 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Glu | Val | Gln | Leu | Gln | Gln | Ser | Gly | Pro | Glu | Leu | Val | Lys | Pro | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ala | Ser | Val | Arg | Met | Ser | Cys | Lys | Ser | Ser | Gly | Tyr | Ile | Phe | Thr | Asp |
|     |     |     | 20  |     |     |     |     | 25  |     |     |     |     | 30  |     |     |
| Phe | Tyr | Met | Asn | Trp | Val | Arg | Gln | Ser | His | Gly | Lys | Ser | Leu | Asp | Tyr |
|     |     |     | 35  |     |     |     |     | 40  |     |     |     |     | 45  |     |     |
| Ile | Gly | Tyr | Ile | Ser | Pro | Tyr | Ser | Gly | Val | Thr | Gly | Tyr | Asn | Gln | Lys |
|     | 50  |     |     |     |     | 55  |     |     |     |     | 60  |     |     |     |     |
| Phe | Lys | Gly | Lys | Ala | Thr | Leu | Thr | Val | Asp | Lys | Ser | Ser | Ser | Thr | Ala |
| 65  |     |     |     |     | 70  |     |     |     |     | 75  |     |     |     |     | 80  |
| Tyr | Met | Glu | Leu | Arg | Ser | Leu | Thr | Ser | Glu | Asp | Ser | Ala | Val | Tyr | Tyr |
|     |     |     |     | 85  |     |     |     |     | 90  |     |     |     |     | 95  |     |
| Cys | Ala | Gly | Ser | Ser | Gly | Asn | Lys | Trp | Ala | Met | Asp | Tyr | Trp | Gly | His |
|     |     |     |     | 100 |     |     |     |     | 105 |     |     |     |     | 110 |     |
| Gly | Ala | Ser | Val | Thr | Val | Ser | Ser | Gly | Ser | Ser | Ser | Ser | Gly | Ser | |
|     |     |     | 115 |     |     |     |     | 120 |     |     |     |     | 125 |     |     |
| Ser | Ser | Ser | Gly | Ser | Asp | Val | Val | Met | Thr | Gln | Thr | Pro | Leu | Ser | Leu |
|     |     |     | 130 |     |     |     |     | 135 |     |     |     |     | 140 |     |     |
| Pro | Val | Ser | Leu | Gly | Asp | Gln | Ala | Ser | Ile | Ser | Cys | Arg | Ser | Ser | Gln |
| 145 |     |     |     |     | 150 |     |     |     |     | 155 |     |     |     |     | 160 |
| Ser | Leu | Val | His | Ser | Asn | Gly | Asn | Thr | Tyr | Leu | Asn | Trp | Tyr | Leu | Gln |
|     |     |     |     | 165 |     |     |     |     | 170 |     |     |     |     | 175 |     |

| | | | | | | | | | | | | | | | | |
|---|---|---|---|---|---|---|---|---|---|---|---|---|---|---|---|---|
|Lys|Ala|Gly|Gln|Ser|Pro|Lys|Leu|Leu|Ile|Tyr|Lys|Val|Ser|Asn|Arg| |
| | | |180| | | |185| | | | |190| | | | |
|Phe|Ser|Gly|Val|Pro|Asp|Arg|Phe|Ser|Gly|Ser|Gly|Ser|Gly|Thr|Asp| |
| | |195| | | |200| | | | |205| | | | | |
|Phe|Thr|Leu|Lys|Ile|Ser|Arg|Val|Glu|Ala|Glu|Asp|Leu|Gly|Ile|Tyr| |
| |210| | | | |215| | | | |220| | | | | |
|Phe|Cys|Ser|Gln|Thr|Thr|His|Val|Pro|Pro|Thr|Phe|Gly|Gly|Gly|Thr| |
|225| | | | |230| | | | |235| | | | |240| |
|Lys|Leu|Glu|Ile|Lys|Arg|Ser|Gly|Gly|Gly|Gly|Cys| | | | | |
| | | | |245| | | | | |250| | | | | | |

( 2 ) INFORMATION FOR SEQ ID NO:5:

( i ) SEQUENCE CHARACTERISTICS:
     ( A ) LENGTH: 739 base pairs
     ( B ) TYPE: nucleic acid
     ( C ) STRANDEDNESS: single
     ( D ) TOPOLOGY: linear ( i i ) MOLECULE TYPE: cDNA ( i x ) FEATURE:
     ( A ) NAME/KEY: CDS
     ( B ) LOCATION: 1..729
     ( D ) OTHER INFORMATION: /product="520C9 sFv polypeptide sequence"

( x i ) SEQUENCE DESCRIPTION: SEQ ID NO:5:

| | | | | | | | | | | | | | | | | |
|---|---|---|---|---|---|---|---|---|---|---|---|---|---|---|---|---|
|GAG|ATC|CAA|TTG|GTG|CAG|TCT|GGA|CCT|GAG|CTG|AAG|AAG|CCT|GGA|GAG|48|
|Glu|Ile|Gln|Leu|Val|Gln|Ser|Gly|Pro|Glu|Leu|Lys|Lys|Pro|Gly|Glu| |
|1| | | |5| | | | |10| | | | |15| | |
|ACA|GTC|AAG|ATC|TCC|TGC|AAG|GCT|TCT|GGA|TAT|ACC|TTC|GCA|AAC|TAT|96|
|Thr|Val|Lys|Ile|Ser|Cys|Lys|Ala|Ser|Gly|Tyr|Thr|Phe|Ala|Asn|Tyr| |
| | | |20| | | | |25| | | | |30| | | |
|GGA|ATG|AAC|TGG|ATG|AAG|CAG|GCT|CCA|GGA|AAG|GGT|TTA|AAG|TGG|ATG|144|
|Gly|Met|Asn|Trp|Met|Lys|Gln|Ala|Pro|Gly|Lys|Gly|Leu|Lys|Trp|Met| |
| | |35| | | | |40| | | | |45| | | | |
|GGC|TGG|ATA|AAC|ACC|TAC|ACT|GGA|CAG|TCA|ACA|TAT|GCT|GAT|GAC|TTC|192|
|Gly|Trp|Ile|Asn|Thr|Tyr|Thr|Gly|Gln|Ser|Thr|Tyr|Ala|Asp|Asp|Phe| |
| |50| | | | |55| | | | |60| | | | | |
|AAG|GAA|CGG|TTT|GCC|TTC|TCT|TTG|GAA|ACC|TCT|GCC|ACC|ACT|GCC|CAT|240|
|Lys|Glu|Arg|Phe|Ala|Phe|Ser|Leu|Glu|Thr|Ser|Ala|Thr|Thr|Ala|His| |
|65| | | | |70| | | | |75| | | | |80| |
|TTG|CAG|ATC|AAC|AAC|CTC|AGA|AAT|GAG|GAC|TCG|GCC|ACA|TAT|TTC|TGT|288|
|Leu|Gln|Ile|Asn|Asn|Leu|Arg|Asn|Glu|Asp|Ser|Ala|Thr|Tyr|Phe|Cys| |
| | | | |85| | | | |90| | | | |95| | |
|GCA|AGA|CGA|TTT|GGG|TTT|GCT|TAC|TGG|GGC|CAA|GGG|ACT|CTG|GTC|AGT|336|
|Ala|Arg|Arg|Phe|Gly|Phe|Ala|Tyr|Trp|Gly|Gln|Gly|Thr|Leu|Val|Ser| |
| | | |100| | | | |105| | | | |110| | | |
|GTC|TCT|GCA|TCG|ATA|TCG|AGC|TCC|TCC|GGA|TCT|TCA|TCT|AGC|GGT|TCC|384|
|Val|Ser|Ala|Ser|Ile|Ser|Ser|Ser|Ser|Gly|Ser|Ser|Ser|Ser|Gly|Ser| |
| | |115| | | | |120| | | | |125| | | | |
|AGC|TCG|AGT|GGA|TCC|GAT|ATC|CAG|ATG|ACC|CAG|TCT|CCA|TCC|TCC|TTA|432|
|Ser|Ser|Ser|Gly|Ser|Asp|Ile|Gln|Met|Thr|Gln|Ser|Pro|Ser|Ser|Leu| |
| | |130| | | | |135| | | | |140| | | | |
|TCT|GCC|TCT|CTG|GGA|GAA|AGA|GTC|AGT|CTC|ACT|TGT|CGG|GCA|AGT|CAG|480|
|Ser|Ala|Ser|Leu|Gly|Glu|Arg|Val|Ser|Leu|Thr|Cys|Arg|Ala|Ser|Gln| |
|145| | | | |150| | | | |155| | | | |160| |
|GAC|ATT|GGT|AAT|AGC|TTA|ACC|TGG|CTT|CAG|CAG|GAA|CCA|GAT|GGA|ACT|528|
|Asp|Ile|Gly|Asn|Ser|Leu|Thr|Trp|Leu|Gln|Gln|Glu|Pro|Asp|Gly|Thr| |
| | | |165| | | | |170| | | | |175| | | |
|ATT|AAA|CGC|CTG|ATC|TAC|GCC|ACA|TCC|AGT|TTA|GAT|TCT|GGT|GTC|CCC|576|

|  |  |  |  |  |  |  |  |  |  |  |  |  |  |  |  |
|---|---|---|---|---|---|---|---|---|---|---|---|---|---|---|---|
| Ile | Lys | Arg | Leu<br>180 | Ile | Tyr | Ala | Thr | Ser<br>185 | Ser | Leu | Asp | Ser | Gly<br>190 | Val | Pro |

| AAA | AGG | TTC | AGT | GGC | AGT | CGG | TCT | GGG | TCA | GAT | TAT | TCT | CTC | ACC | ATC | 624 |
|---|---|---|---|---|---|---|---|---|---|---|---|---|---|---|---|---|
| Lys | Arg<br>195 | Phe | Ser | Gly | Ser | Arg<br>200 | Ser | Gly | Ser | Asp | Tyr | Ser<br>205 | Leu | Thr | Ile |  |

| AGT | AGC | CTT | GAG | TCT | GAA | GAT | TTT | GTA | GTC | TAT | TAC | TGT | CTA | CAA | TAT | 672 |
|---|---|---|---|---|---|---|---|---|---|---|---|---|---|---|---|---|
| Ser | Ser<br>210 | Leu | Glu | Ser | Glu | Asp<br>215 | Phe | Val | Val | Tyr | Tyr<br>220 | Cys | Leu | Gln | Tyr |  |

| GCT | ATT | TTT | CCG | TAC | ACG | TTC | GGA | GGG | GGG | ACC | AAC | CTG | GAA | ATA | AAA | 720 |
|---|---|---|---|---|---|---|---|---|---|---|---|---|---|---|---|---|
| Ala<br>225 | Ile | Phe | Pro | Tyr<br>230 | Thr | Phe | Gly | Gly | Gly<br>235 | Thr | Asn | Leu | Glu | Ile<br>240 | Lys |  |

| CGG | GCT | GAT | TAATCTGCAG |  |  |  |  |  |  |  |  |  |  |  | 739 |
|---|---|---|---|---|---|---|---|---|---|---|---|---|---|---|---|
| Arg | Ala | Asp |  |  |  |  |  |  |  |  |  |  |  |  |  |

( 2 ) INFORMATION FOR SEQ ID NO:6:

( i ) SEQUENCE CHARACTERISTICS:
        ( A ) LENGTH: 243 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Glu<br>1 | Ile | Gln | Leu | Val<br>5 | Gln | Ser | Gly | Pro | Glu<br>10 | Leu | Lys | Lys | Pro | Gly<br>15 | Glu |
|---|---|---|---|---|---|---|---|---|---|---|---|---|---|---|---|
| Thr | Val | Lys | Ile<br>20 | Ser | Cys | Lys | Ala | Ser<br>25 | Gly | Tyr | Thr | Phe | Ala<br>30 | Asn | Tyr |
| Gly | Met | Asn<br>35 | Trp | Met | Lys | Gln | Ala<br>40 | Pro | Gly | Lys | Gly | Leu<br>45 | Lys | Trp | Met |
| Gly | Trp<br>50 | Ile | Asn | Thr | Tyr | Thr<br>55 | Gly | Gln | Ser | Thr | Tyr<br>60 | Ala | Asp | Asp | Phe |
| Lys<br>65 | Glu | Arg | Phe | Ala | Phe<br>70 | Ser | Leu | Glu | Thr | Ser<br>75 | Ala | Thr | Thr | Ala | His<br>80 |
| Leu | Gln | Ile | Asn | Asn<br>85 | Leu | Arg | Asn | Glu | Asp<br>90 | Ser | Ala | Thr | Tyr | Phe<br>95 | Cys |
| Ala | Arg | Arg | Phe<br>100 | Gly | Phe | Ala | Tyr | Trp<br>105 | Gly | Gln | Gly | Thr | Leu<br>110 | Val | Ser |
| Val | Ser | Ala | Ser<br>115 | Ile | Ser | Ser | Ser<br>120 | Ser | Gly | Ser | Ser | Ser<br>125 | Ser | Gly | Ser |
| Ser | Ser<br>130 | Ser | Gly | Ser | Asp | Ile<br>135 | Gln | Met | Thr | Gln | Ser<br>140 | Pro | Ser | Ser | Leu |
| Ser<br>145 | Ala | Ser | Leu | Gly | Glu<br>150 | Arg | Val | Ser | Leu | Thr<br>155 | Cys | Arg | Ala | Ser | Gln<br>160 |
| Asp | Ile | Gly | Asn | Ser<br>165 | Leu | Thr | Trp | Leu | Gln<br>170 | Gln | Glu | Pro | Asp | Gly<br>175 | Thr |
| Ile | Lys | Arg | Leu<br>180 | Ile | Tyr | Ala | Thr | Ser<br>185 | Ser | Leu | Asp | Ser | Gly<br>190 | Val | Pro |
| Lys | Arg | Phe<br>195 | Ser | Gly | Ser | Arg | Ser<br>200 | Gly | Ser | Asp | Tyr | Ser<br>205 | Leu | Thr | Ile |
| Ser | Ser<br>210 | Leu | Glu | Ser | Glu | Asp<br>215 | Phe | Val | Val | Tyr | Tyr<br>220 | Cys | Leu | Gln | Tyr |
| Ala<br>225 | Ile | Phe | Pro | Tyr<br>230 | Thr | Phe | Gly | Gly | Gly<br>235 | Thr | Asn | Leu | Glu | Ile<br>240 | Lys |
| Arg | Ala | Asp |  |  |  |  |  |  |  |  |  |  |  |  |  |

( 2 ) INFORMATION FOR SEQ ID NO:7:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: protein ( i x ) FEATURE:
    ( A ) NAME/KEY: Protein
    ( B ) LOCATION: 1..15
    ( D ) OTHER INFORMATION: /note= "Linker 1"

( x i ) SEQUENCE DESCRIPTION: SEQ ID NO:7:

```
Gly Gly Gly Gly Ser Gly Gly Gly Gly Ser Gly Gly Gly Gly Ser
 1               5                  10                  15
```

( 2 ) INFORMATION FOR SEQ ID NO:8:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..15
        ( D ) OTHER INFORMATION: /note= "LINKER 2"

( x i ) SEQUENCE DESCRIPTION: SEQ ID NO:8:

```
Ser Ser Ser Ser Gly Ser Ser Ser Ser Gly Ser Ser Ser Ser Gly
 1               5                  10                  15
```

( 2 ) INFORMATION FOR SEQ ID NO:9:

( i ) SEQUENCE CHARACTERISTICS:
        ( A ) LENGTH: 2 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..2
        ( D ) OTHER INFORMATION: /note= "C-Terminal Tail (Ser-Cys)"

( x i ) SEQUENCE DESCRIPTION: SEQ ID NO:9:

```
Ser Cys
 1
```

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..5
        ( D ) OTHER INFORMATION: /note= "C-Terminal Tail
        (Gly-Gly-Gly-Gly-Cys)"

( x i ) SEQUENCE DESCRIPTION: SEQ ID NO:10:

```
Gly Gly Gly Gly Cys
```

(2) INFORMATION FOR SEQ ID NO:11:

(i) SEQUENCE CHARACTERISTICS:
      (A) LENGTH: 11 amino acids
      (B) TYPE: amino acid
      (C) STRANDEDNESS: single
      (D) TOPOLOGY: linear (ii) MOLECULE TYPE: protein (ix) FEATURE:
      (A) NAME/KEY: Protein
      (B) LOCATION: 1..11
      (D) OTHER INFORMATION: /note= "C-Terminal Tail
      (His-His-His-His-His-His-Gly-Gly-Gly-Gly-Cys)"

(xi) SEQUENCE DESCRIPTION: SEQ ID NO:11:

His  His  His  His  His  His  Gly  Gly  Gly  Gly  Cys
      1                   5                        10

BIOSYNTHETIC BINDING PROTEINS FOR IMMUNOTARGETING

CROSS REFERENCE TO RELATED APPLICATIONS

This application is a divisional of application U.S. Ser. No. 08/133,804, filed Oct. 7, 1993, now U.S. Pat. No. 5,534,254, which is a continuation-in-part of application U.S. Ser. No. 07/831,967, filed Feb. 6, 1992, now abandoned, the disclosure of which is incorporated herein by reference. Related applications include: U.S. Ser. No. 08/356,786 filed Dec. 12, 1994 which is a continuation of U.S. Ser. No. 07/831,967, now abandoned, filed Feb. 6, 1992; U.S. Ser. No. 08/461,386 filed Jun. 5, 1995, which is a divisional of U.S. Ser. No. 08/133,804, filed Oct. 7, 1993, now U.S. Pat. No. 5,534,254, which is a continuation-in-part of U.S. Ser. No. 07/831,967, filed Feb. 6, 1992, now abandoned; U.S. Ser. No. 08/462,641 filed Jun. 5, 1995, which is a continuation of U.S. Ser. No. 08/133,804, filed Oct. 7, 1993, now U.S. Pat. No. 5,534,254, which is a continuation-in-part of U.S. Ser. No. 07/831,967, filed Feb. 6, 1992, now abandoned; and U.S. Ser. No. 08/462,295 filed Jun. 5, 1995, now abandoned, which is a continuation of U.S. Ser. No. 08/133,804, filed Oct. 7, 1993, now U.S. Pat. No. 5,534,254, which is a continuation-in-part of U.S. Ser. No. 07/831,967, filed Feb. 6, 1992, now abandoned.

The U.S. Government may have certain rights in the invention described herein, by virtue of National Institutes of Health Grant No. UO1 CA51880.

FIELD OF THE INVENTION

This invention relates in general to novel biosynthetic compositions of matter having particular utility as in vivo targeting agents and more specifically, to biosynthetic dimeric constructs of single-chain binding proteins (sFv), conjugates thereof, and to methods for their production.

BACKGROUND OF THE INVENTION

The development of murine monoclonal antibodies and their proteolytic Fab fragments has raised interest in their utility as diagnostic and therapeutic reagents for in vivo imaging and drug targeting. However, successful in vivo targeting of radionuclides, drugs or toxins using 150 kD intact antibodies or their 50 kD Fab fragments (an antibody fragment consisting of one light chain and approximately half of the heavy chain held together by a single disulfide bond) have been restricted by the limited penetration of these molecules from the vasculature into the tissues of interest, and by their slow clearance rates in vivo, which for IgG leads to behavior that requires several days to clear the background enough for imaging to be possible. Other disadvantages of the intact antibodies or their Fab fragments include: their immunogenicity when prepared from different species, their non-specific binding to many normal tissues and organs, and the fact that they contain multiple proteolytic cleavage sites which result in their degradation during their circulation in vivo.

Although Fv fragments, which consist of one $V_H$ and one $V_L$ domain held together by noncovalent interactions, form the minimal region of an antibody that contains a complete antigen combining site, dissociation of the $V_H$ and $V_L$ domains in vivo can preclude their use as therapeutic or imaging agents. Although Moore et al., (U.S. Pat. No. 4,642,334) and Glockshuber et al., (1990, Biochem. 29, 1362–1367) disclose attempts to stabilize these Fv fragments with engineered intermolecular disulfide bonds, monovalent 50 kD Fab and Fab' fragments have, until recently, been the smallest proteins available for effective immunotargeting.

Recently, single-chain Fv (sFv) polypeptide chains of about 27 kD have been developed containing covalently linked $V_H$-$V_L$ polypeptides. The $V_H$- and $V_L$-domains are connected by a polypeptide linker. The resulting sFv polypeptide chains are also referred to in the art as biosynthetic antibody binding sites or BABS and preferably are encoded by a single DNA sequence. For a detailed description of these biosynthetic polypeptide chains see for example, Huston et al., 1988, Proc. Nat. Aca. Sci. USA 85: 5879–5883 or U.S. Pat. Nos. 5,091,513 and 5,132,405, all of which are hereby incorporated by reference. The sFv polypeptide chains provide attractive alternatives to intact immunoglobulins and Fab fragments due to their small size and their stability at concentrations that typically promote dissociation of natural Fv fragments. U.S. Pat. Nos. 5,091,513 and 5,132,405; Huston et al., ((1991) Methods in Enzymology 203: 46–88; Huston et al (1993) Int. Rev. Immunol. 10: 195–217) disclose the utility of sFv polypeptides, as well as single chain constructs synthesized from single DNA sequences, which may further comprise ancillary effector proteins, such as a second sFv or a cytotoxic agent.

Pack et al. ((1992) Biochem 31: 1579–1584) disclose the construction of "mini-antibodies". The mini-antibodies are sFv polypeptide chains which also include an "oligomerization domain" at their C-termini, separated from the sFv by a hinge region. The oligomerization domains comprise self-associating α-helices, for example, leucine zippers, that can be further stabilized by additional disulfide bonds. The domains are designed to be compatible with vectorial folding across a membrane, a process thought to facilitate in vivo folding of the polypeptide into a functional binding protein.

PCT application PCT/US92/09965, published Jun. 10, 1993 also discloses the construction of bivalent sFv constructs, including crosslinked dimers. However, the pharmacokinetic properties of these constructs or those disclosed by Pack et al. are not measured in vivo.

PCT application PCT/US92/07986, published Apr. 1, 1993 discloses bifunctional (Fab')$_2$ molecules composed of two Fab' monomers linked through cysteine amino acids located at the C-terminus of the first constant domain of each heavy chain. PCT application PCT/US92/10140, published Jun. 10, 1993 also discloses bifunctional (Fab')$_2$ dimers which, in addition to the cysteine residues located in the hinge region, also contain C-terminal leucine zipper domains that further stabilize the (Fab')$_2$ dimers. In both cases, the resulting (Fab')$_2$ dimers ($\geq 100$ kD in size), although smaller than intact immunoglobulins, are significantly larger than sFv polypeptides and are anticipated to have slower tissue biodistribution and clearance rates following in vivo administration.

Cumber et al. disclose the generation of (Fv-Cys)$_2$ heterodimers by chemically crosslinking two $V_H$-cys domains together (Cumber et al., 1992, J. Immunology 149B: 120–126). Although the crosslinked $V_H$ chains appear to be stable, dissociation of the $V_L$ polypeptides from each Fv reduces the pharmacological value of these constructs in vivo.

It is an object of the instant invention to provide biosynthetic constructs having enhanced pharmacokinetic properties as in vivo targeting agents. In particular, it is an object of this invention to provide biocompatible constructs having accelerated in vivo biodistribution and body clearance rates than that of antibodies or antibody fragments. It is another object of the invention to provide biosynthetic constructs having enhanced avidity in vivo, including enhanced target tissue specificity and target tissue retention. Yet another object is to provide dimeric biosynthetic constructs having improved tissue imaging and drug targeting properties in vivo. Still another object is to provide diagnostic and therapeutic formulations comprising these constructs, having particular utility in the diagnosis and treatment of malignancies. Still another object is to provide constructs having enhanced pharmacokinetic properties as in vivo targeting agents, particularly as in vivo imaging agents, for ovarian and breast tumor tissue.

These and other objects and features of the invention will be apparent from the description, figures and claims which follow.

SUMMARY OF THE INVENTION

In its broadest aspect, the invention features a formulation for targeting an epitope on an antigen expressed in a mammal, where the formulation contains a pharmaceutically acceptable carrier in combination with a biosynthetic construct for binding at least one preselected antigen. The dimeric construct has particular utility in diagnostic and therapeutic applications in vivo.

The invention features the synthesis and use of monomers and dimers of polypeptide constructs belonging to the class of proteins known as single-chain Fv (sFv) polypeptides. The sFv proteins described herein have superior in vivo pharmacokinetic properties, including accelerated tissue biodistribution and clearance rates relative to either intact IgG, (Fab)$_2$ dimers or Fab.

The dimeric biosynthetic construct of the invention contains two sFv polypeptide chains defined herein as follows. Each sFv polypeptide chain comprises an amino acid sequence defining at least two polypeptide domains. These domains are connected by a polypeptide linker spanning the distance between the C-terminus of one domain and the N-terminus of the other. The amino acid sequence of each domain includes complementarity determining regions (CDRs) interposed between framework regions (FRs) where the CDRs and FRs of each polypeptide chain together define a binding site immunologically reactive with a preselected antigen. Additionally, each biosynthetic binding site polypeptide chain can have an amino acid sequence peptide bonded and thus contiguous with the C-terminus of each polypeptide chain, referred to herein as a "C-terminal tail" sequence. The term "sFv'" refers hereinafter, to an sFv molecule containing such a C-terminal tail sequence. This tail sequence preferably does not contain an α-helical motif that self-associates with another polypeptide chain of similar sequence but still contains a means for covalently crosslinking two such polypeptide chains together. When the two sFv' polypeptide chains are crosslinked together, the resulting dimeric construct has a conformation that permits the independent binding of a preselected antigen or antigens to the binding site of each polypeptide chain in vitro and in vivo. The resulting dimeric constructs have superior in vivo pharmacokinetic properties that include significantly enhanced avidity, including enhanced target tissue retention and/or antigen localization properties, as compared with intact IgG, Fab, (Fab)$_2$ dimers or monomeric sFv.

As will be appreciated by those having ordinary skill in the art, the sequence referred to herein generally as a "C-terminal tail" sequence, peptide bonded to the C-terminus of an sFv and comprising means for crosslinking two sFv polypeptide chains, alternatively may occur at the N-terminus of an sFv ("N-terminal tail") or may comprise part of the, polypeptide linker spanning the domains of an individual sFv. The dimeric species created by the crosslinking of sFvs having these alternative "tail" sequences also are contemplated to have a conformation permitting the in vivo binding of a preselected antigen by the binding sites of each of the sFv polypeptide chains. Accordingly, descriptions of how to make and use sFv' monomers and dimers comprising a C-terminal tail sequence are extended hereby to include sFv monomers and dimers wherein the tail sequence having crosslinking means occurs at the N-terminus of an sFv or comprises part of the polypeptide linker sequence.

In one embodiment, both polypeptide chains bind the same epitope on a preselected antigen, and the resulting dimeric construct is termed a "homodimer." In another embodiment, the polypeptide chains bind different epitopes on a preselected antigen and the resulting dimeric construct is termed a "heterodimer." In still another embodiment, the two polypeptide chains bind different epitopes on two different, preselected antigens.

The term "epitope", as used herein, refers to a portion of an antigen that makes contact with a particular antibody or antibody analogue. In a typical protein, it is likely that any residue accessible from the surface can form part of one or more antigenic determinants. The term "antigen", as used herein, refers to a molecule that can elicit an immune response and that can react specifically with corresponding antibodies or antibody analogues.

The term "domain", as used herein, refers to an amino acid sequence that folds into a single globular region in its native conformation, and which may exhibit discrete binding or functional properties. The term "polypeptide linker", as used herein, refers to an amino acid sequence that links the C-terminus of one domain to the N-terminus of the other domain, while still permitting the two domains to maintain their proper physiologically active binding conformations. In a particular aspect of the invention, the currently preferred polypeptide linkers that connect the C-terminus of one domain to the N-terminus of the other domain include part or all of amino acid sequence ((Gly)$_4$ Ser)$_3$ set forth in the SEQ. ID. NO.: 7, or ((Ser)$_4$ Gly)$_3$ as set forth in SEQ. ID. NO.: 8.

The amino acid sequence of each of the polypeptide domains includes complementarity determining regions interposed between framework regions. The term "complementarity determining regions" or "CDRs", as used herein, refer to amino acid sequences which together define the binding affinity and specificity of the natural Fv region of a native immunoglobulin binding site, or a synthetic polypeptide which mimics this function. CDRs are not necessarily wholly homologous to hypervariable regions of natural Fv molecules, and also may include specific amino acids or amino acid sequences which flank the hypervariable region and have heretofore been considered framework not directly determinative of complementarity. The term "framework regions" or "FRs", as used herein, refers to amino acid sequences which are found naturally occurring between CDRs in immunoglobulins. These FR sequences may be derived in whole or part from the same immunoglobulin as the CDRs, or in whole or part from a different immunoglobulin. For example, in order to enhance biocompatibility of an sFv to be administered to a human, the FR sequences can be derived from a human immunoglobulin and so the resulting humanized sFv will be less immunogenic than a murine monoclonal antibody.

The amino acid sequence of each variable domain includes three CDRs interspersed between four FRs. The two polypeptide domains that define an sFv molecule contain CDRs interspersed between FRs which together form a binding site immunologically reactive with a preselected antigen. The term "immunologically reactive", as used herein, refers to the noncovalent interactions of the type that occur between an immunoglobulin molecule and an antigen for which the immunoglobulin is specific. As used herein, the term "avidity" describes the stability of a complex formed by a multivalent antibody or antibody analogue, with its binding conjugate. Also as used herein, the term "apparent avidity" describes the stability of a complex formed by an antibody or an antibody analogue with its binding conjugate as determined by in vivo immunolocalization studies.

In a preferred aspect of the invention, the CDRs of the polypeptide chain can have an amino acid sequence substantially homologous with at least a portion of the amino acid sequence of CDRs from a variable region of an immunoglobulin molecule from a first species, together with FRs that are substantially homologous with at least a portion of the amino acid sequence of FRs from a variable region of an immunoglobulin molecule from a second species. Preferably, the first species is mouse and the second species is human. The CDR sequences in the sFv' polypeptides are preferably substantially homologous to an immunoglobulin CDR retaining at least 70%, or more preferably 80% or 90%, of the amino acid sequence of the immunoglobulin CDR, and also retains the immunological binding properties of the immunoglobulin.

Each sFv' molecule has a C-terminal polypeptide tail that has a non-self-associating structure and contains at least one crosslinking means. Useful crosslinking means include derivatizable amino acid side chains, particularly those selected from the group consisting of cysteine, lysine, arginine, histidine, glutamate, aspartate, and derivatives and modified forms thereof. In a preferred aspect of the invention, cysteine amino acids are incorporated into the C-terminal tail sequences as the crosslinking means. In another aspect of the invention, the crosslinking means includes one or more amino acids that can be posttranslationally modified. For example, the crosslinking means can include one or more glycosylation sites, wherein the incorporated carbohydrate moieties can be crosslinked in vitro. Preferred glycosylation sequences include Asn-Xaa-Thr and Asn-Xaa-Ser, where Xaa can be any amino acid, wherein the carbohydrate is typically N-linked to asparagine or O-linked to serine or threonine.

Additionally, the tail also may comprise an amino acid sequence that defines a metal ion chelation motif, and which facilitates purification of the sFv' monomers by metal ion affinity chromatography, such as the $IMAC^{2+}$ chromatography system. Furthermore, chelation motifs can be used for binding detectable moieties, such as Technetium$^{-99m}$ ($^{99m}$Tc) for in vivo imaging. Preferred examples of useful C-terminal tail amino acid sequences wherein the crosslinking means is provided by the sulfhydryl group of a cysteine, include: Ser-Cys; (Gly)$_4$-Cys; and (His)$_6$-(Gly)$_4$-Cys; set forth in the Sequence Listing as SEQ. ID. NOS.: 9, 10 and 11, respectively. The (Gly)$_4$-Cys sequence facilitates the coordination of $^{99m}$Tc by this tail.

In the present invention, monomeric sFv' molecules can be coupled together through the crosslinking means in the C-terminal tails to form either homo- or heterodimeric (sFv')$_2$ species. The term "sFv coupler", as used herein, refers to the chemical bridge that links two sFv' polypeptide chains together to form a dimeric species. In a preferred aspect of the invention, where the crosslinking means is a cysteine residue, the linkage is by a disulfide bond. Alternatively, sulfhydryl-specific homobifunctional crosslinking reagents, such as bismaleimidohexane, or heterobifunctional crosslinking reagents, can be used to join the two sFv' molecules together. sFv couplers of preselected length also can be designed to limit interaction between the two sFv' polypeptide chains or to optimize binding of two preselected antigens, including, for example, multiple copies of a receptor expressed on a cell surface in a mammal. An example of such a variable length coupler includes the bismaleimidocaproyl amino acid (MCA) synthetic peptide bridge. Although, in a preferred aspect of the invention a GlySer$_3$Gly$_2$Ser$_3$Lys peptide spacer is used, in theory, any amino acid sequence can be introduced into this type of chemical bridge with a variety of reactive moieties at either end. Consequently, it is possible to design specific linkage groups that can have a predetermined length and flexibility. If a substantially inflexible coupler is desired, then for instance, a polylysine or polyproline peptide may be used. Another benefit of the MCA linkers over many other commercially available linkers is that they are soluble in water. Moreover, the chemical bridge also may be created to enhance the imaging or therapeutic properties of the construct in vivo (vide infra). As will be appreciated by those having ordinary skill in the art, the separation distance between, arid interaction of, the sFv' monomers in a dimeric construct of the invention also can be modulated by the judicious choice of amino acids in the tail sequences themselves.

The dimeric constructs of this invention preferably target a pharmacologically active drug (or other ancillary protein) to a site of interest utilizing the bivalent capability of the dimer. Examples of pharmacologically active drugs include molecules that inhibit cell proliferation and cytotoxic agents that kill cells. The term "cytotoxic agent", as used herein, refers to any molecule that kills cells, and includes anticancer therapeutic agents such as doxorubicin. Other, useful molecules include toxins, for instance, the toxic portion of the Pseudomonas exotoxin, phytolaccin, ricin, ricin A chain, or diptheria toxin, or other related proteins known as ricin A chain-like ribosomal inhibiting proteins, i.e., proteins capable of inhibiting protein synthesis at the level of the ribosome, such as pokeweed antiviral protein, gelonin, and barley ribosomal protein inhibitor.

In such cases, one sFv' can be immunologically reactive with a binding site on an antigen at the site of interest, and the second sFv' in the dimer can be immunologically reactive with a binding site on the drug to be targeted. Alternatively, the construct may bind one or more antigens at the the site of interest and the drug to be targeted is otherwise associated with the dimer, for example, crosslinked to the chemical bridge itself. The biosynthetic dimeric constructs of this invention also may be used as part of human therapies to target cytotoxic cells such as cytotoxic T-lymphocytes, or pharmacologically active drugs to a preselected site. A bispecific (sFv')$_2$ heterodimer having specificity for both a tumor antigen and a CD3 antigen, the latter of which is present on cytotoxic T-lymphocytes, thus could mediate antibody dependent cellular cytotoxicity (ADCC) or cytotoxic T-lymphocyte-induced lysis of the tumor cells.

Still another bispecific dimeric construct having cytotoxic properties is a bispecific construct with one sFv' capable of targeting a tumor cell and the second sFv' having catalytic properties that binds an inactive drug, subsequently converting it into an active compound (see for example, U.S. Pat. No. 5,219,732). Such a construct would be capable of inducing the formation of a toxic substance in situ. For example, a catalytic sFv' molecule having β-lactamase-like activity can be designed to bind and catalyze the conversion of an inactive lactam derivative of doxorubicin into its active form. Here the bispecific dimer, having binding affinities for both the preselected antigen and the inactive-lactam derivative, is administered to an individual and allowed to accumulate at the desired location. The inactive and non-toxic cytotoxin-lactam derivative then is administered to the individual. Interaction of the derivative with the bispecific (sFv')$_2$ heterodimer at the site of interest releases the active form of the drug in situ, enhancing both the cytotoxicity and specificity of the drug.

The homo- and heterodimeric biosynthetic constructs also may include a detectable moiety bound either to the polypeptide chain, e.g., to the tail sequence, or to the chemical coupler. The term "detectable moiety", as used herein, refers to the moiety bound to or otherwise complexed with the construct and which can be detected external to, and at a distance from, the site of the complex formation, to permit the imaging of cells or cell debris expressing a preselected antigen. Preferable detectable moieties for imaging include radioactive atoms such as Technetium-99m ($^{99m}$Tc), a gamma emitter with a half-life of about 6 hours. Non-radioactive moieties useful for in vivo magnetic resonance imaging applications include nitroxide spin labels as well as lanthanide and transition metal ions which induce proton relaxation in situ. In addition to immunoimaging, the complexed radioactive moieties also may be used in standard radioimmunotherapy protocols to destroy the targeted cell. Preferable nucleotides for high dose radioimmunotherapy include radioactive atoms such as, $^{90}$Yttrium ($^{90}$Yt), $^{131}$Iodine ($^{131}$I) or Indium ($^{111}$In).

The sFv, sFv' and (sFv')$_2$ constructs disclosed herein have particular utility as in vivo targeting agents of tumor antigens, including antigens characteristic of breast and ovarian malignancies, such as the c-erbB-2 or c-erbB-2 related antigens. Accordingly, these constructs have particular utility in diagnostic applications as imaging agents of malignant cells, and in therapeutic applications as targeting agents for cytotoxins and other cancer therapeutic agents. In one preferred aspect of the invention, the CDRs of the sFv or sFv' polypeptide chain have an amino acid sequence substantially homologous with the CDRs of the variable region of any one of the following monoclonal antibodies: 741F8, 520C9, and 454C11, all of which bind to c-erbB-2 or c-erbB-2-related antigens. Exemplary sFv' and sFv sequences having CDRs corresponding to the monoclonal antibodies 741F8 and 520C9 are set forth in the Sequence Listing SEQ. ID. NOS.: 1 and 5, respectively.

The term "c-erbB-2" refers to a protein antigen that is an approximately 200 kD acidic glycoprotein having an isoelectric point of about 5.3 and having an extracellular domain overexpressed on the surface of tumor cells, such as breast and ovarian tumor cells in about 25% of cases of breast and ovarian cancer. A "c-erbB-2-related tumor antigen" is a protein located on the surface of tumor cells, such as breast and ovarian tumor cells and which is antigenically related to the c-erbB-2 antigen. That is, the related antigen can be bound by an immunoglobulin that is capable of binding the c-erbB-2 antigen (e.g. 741F8, 520C9, and 454C11 antibodies. Related antigens also include antigens comprising an amino acid sequence that is at least 80% homologous, preferably 90% homologous, with the amino acid sequence of c-erbB-2 or an amino acid sequence encoded by a DNA that hybridizes under stringent conditions with a nucleic acid sequence encoding c-erbB-2. As used herein, stringent hybridization conditions are those set forth in Sambrook, et al., 1989, *Molecular Cloning; A Laboratory Manual* 2nd ed. Cold Spring Harbor Press wherein the hybridization conditions, for example, include 50% formamide, 5x Denhardt's Solution, 5xSSC, 0.1% SDS and 100 μg/ml denatured salmon sperm DNA and the washing conditions include 2xSSC, 0.1% SDS at 37° C. followed by 1xSSC, 0.1% SDS at 68° C. An example of a c-erbB-2-related antigen is the receptor for the epidermal growth factor.

In one embodiment, the biosynthetic antibody binding site is a humanized hybrid molecule which includes CDRs from the mouse 741F8 antibody interposed between FRs derived from one or more human immunoglobulin molecule. The CDRs that bind to the c-erbB-2 epitope can be found in the amino acid residue numbers 31–37, 52–68, 101–110, 159–169, 185–191 and 224–233 in SEQ ID NOS.: 1 and 2. The hybrid molecule thus contains binding sites which are highly specific for the c-erbB-2 antigen or c-erbB-2 related antigens held in proper immunochemical binding conformation by human FR amino acid sequences, which are less likely to be recognized as foreign by the human body.

The dimeric (sFv')$_2$ construct can either be homodimeric, wherein the CDR sequences on both monomers define the same binding site, or heterodimeric, wherein the CDR sequences of each sFv' monomer define a different binding site. An example of an (sFv')$_2$ heterodimer described herein having specificity for both c-erbB-2 and digoxin epitopes can be generated by combining the anti-c-erbB-2 sFv', shown in SEQ. ID. NOS.: 1 and 2 with the anti-digoxin sFv', shown in SEQ. ID. NOS.: 3 and 4. The CDRs that bind to the digoxin epitope can be derived from the anti-digoxin murine monoclonal antibody 26-10 (Huston et al., 1988, *Proc. Nat. Acad. Sci. USA* 85: 5879–5883) and can be found in the amino acid residue numbers 32 through 36, 48 through 65, 101 through 107, 157 through 170, 188 through 194 and 229 through 234 in the Sequence Listing as SEQ. ID. NOS.: 3 and 4.

Radioimaging or radioimmunotherapy of tumor tissues and malignant cells are preferred aspects of this invention. Overexpression of tumor antigens such as c-erbB-2 and related cell surface antigens in malignant cells allows imaging of the malignant cell or tissue, whether it is well localized, has undergone metastasis or is exposed following cell lysis. The imaging method includes the steps of administering to a mammal a formulation comprising an sFv' or (sFv')$_2$ dimeric construct having specificity for the antigen tumor and containing a detectable moiety at a concentration sufficient to permit extracorporeal detection of the construct bound to the tumor antigen; and then detecting the biosynthetic construct bound to the tumor antigen. The formulation can be used to particular advantage in gamma scintigraphy or magnetic resonance imaging. Overexpression of c-erbB-2 or related receptors on malignant cells thus allows targeting of sFv' species to the tumor cells, whether the tumor is well-localized or metastatic. In addition, internalization of an sFv-toxin fusion protein permits specific destruction of tumor cells bearing the overexpressed c-erbB-2 or related antigen.

The present invention discloses monomeric and dimeric biosynthetic constructs having enhanced properties as in vivo targeting agents when compared with intact monoclonal antibodies or their Fab fragments. The dimeric biosynthetic constructs of the invention also permit the in vivo targeting of an epitope on an antigen with greater apparent avidity, including greater tumor specificity, tumor localization and tumor retention properties than that of the Fab fragment having the same CDRs as the construct. Furthermore, the dimeric constructs also permit the in vivo targeting of an epitope on an antigen with a greater apparent avidity, including greater tumor localization and tumor retention properties, than either of the monomeric polypeptides individually.

The invention also includes methods for producing the homo- and heterodimeric biosynthetic constructs, which include the steps of designing, constructing, expressing, purifying, and refolding the monomeric sFv' polypeptide chains in vitro, followed by joining two polypeptide chains together through the crosslinking means in the C-terminal tail sequence, without relying on the tail structure to otherwise assist in dimer formation or enhance transport across a membrane. The invention also includes methods for imaging a preselected antigen in a mammal expressing the preselected antigen. The antigen may be expressed on a cell surface or may be released as part of the cell debris from a dying cell.

The foregoing and other objects, features and advantages of the present invention will be made more apparent from the following detailed description of the invention.

BRIEF DESCRIPTION OF THE DRAWINGS

The foregoing and other objects of this invention, the various features thereof, as well as the invention itself, will be more fully understood from the following description, when read together with the accompanying drawings:

FIG. 4 lists in tabular form the tumor:organ ratios calculated for various sF and sFv' species injected into tumor-containing mice;

FIG. 5 lists in tabular form the percentage of injected dose localized to tumor tissue for various sFv and sFv's species.

DETAILED DESCRIPTION OF THE INVENTION

Figure 1A:
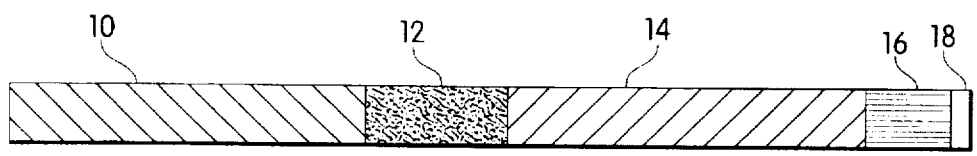
FIG. 1A is a schematic representation of a DNA construct encoding the sFv' biosynthetic binding protein of the invention.

It has been discovered that intravenously administered single-chain Fv (sFv) proteins exhibit superior in vivo pharmacokinetic properties relative to intact monoclonal antibodies (IgG), (Fab)$_2$ dimers or Fab fragments. These pharmacokinetic properties include accelerated rates of tissue biodistribution, enhanced target tissue specificity, and exceptionally fast clearance rates. The sFv constructs can be designed to bind to preselected antigens and to have particular utility for in vivo immunoimaging and immunotherapy applications. In addition, it also has been discovered that dimeric forms of the constructs, which do not rely on self-associating tail sequences for dimerization or transport across a membrane, can be easily prepared and have improved target tissue localization properties, target tissue retention properties and/or avidity for their targets in vivo, relative to monomeric sFv', Fab fragments or intact IgG.

In its broadest aspect, the invention features a formulation for targeting an epitope on an antigen expressed in a mammal. The formulation contains a pharmaceutically acceptable carrier in combination with a dimeric biosynthetic construct for binding at least one preselected antigen. The preselected antigen either may be an antigen expressed on the surface of a cell or an intracellular component exposed upon lysis of the cell. The sFv, sFv' and (sFv')$_2$ constructs disclosed herein have particular utility as in vivo targeting agents for detecting malignant cells in a mammal. In a particularly useful embodiment, the constructs disclosed can be used to target the c-erbB-2 or c-erbB-2-related antigens which are overexpressed in certain breast and ovarian cancers. In another embodiment, radioimmunotargeting using radiolabeled (sFv')$_2$ constructs will be useful for therapeutic as well as diagnostic applications.

Provided below are detailed descriptions of biosynthetic sFv, sFv' and (sFv')$_2$ dimers, useful in the compositions and methods of the invention, together with methods for their construction and administration. Also provided are numerous, non-limiting examples which demonstrate the suitability of these constructs as in vivo targeting reagents for diagnostic and therapeutic applications. More specifically, the examples demonstrate: the construction and expression of sFv polypeptides (Example 1); the renaturation, dimerization and purification of sFv' proteins (Example 2); and the immunoreactivity of the monomeric and dimeric sFv proteins (Example 3).

Construction of Biosynthetic Single-Chain Fv Proteins

Each of the sFv and sFv' proteins have amino acid sequences that define at least two polypeptide domains. The polypeptide domains are connected by a polypeptide linker spanning the distance between the C-terminus of one domain and the N-terminus of the other. The amino acid sequence of each domain includes complementarity determining regions (CDRs) interposed between framework regions (FRs), where the CDRs and FRs of each polypeptide chain together define a binding site immunologically reactive with a preselected antigen.

In the case of the sFv' proteins, each polypeptide chain has an additional C-terminal tail amino acid sequence having a substantially non-self-associating structure. More specifically, this is a sequence that does not interact appreciably with a similar sequence under physiological conditions, as is the case for example with the α-helical leucine zipper motifs found in DNA binding proteins. Each tail sequence also contains a means for crosslinking two such sFv' polypeptide chains together to form an (sFv')$_2$ dimer. The resulting (sFv')$_2$ dimers have conformations which permit the in vivo binding of the preselected antigen by the binding sites of each of the polypeptide chains.

Figure 1B:
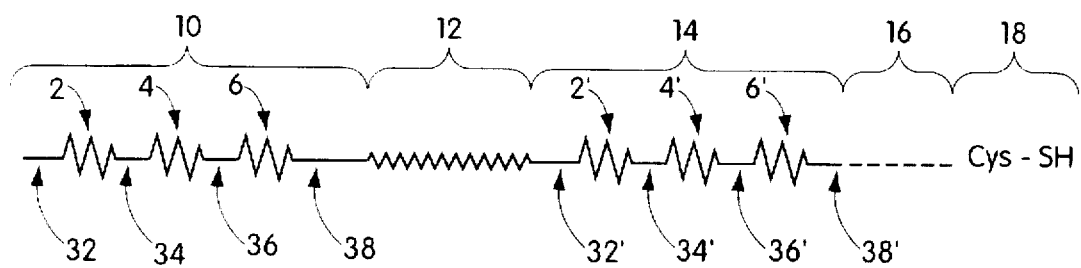
FIG. 1B is a schematic representation of the polypeptide chain encoded by the DNA construct in FIG. 1A.
Figure 2A:
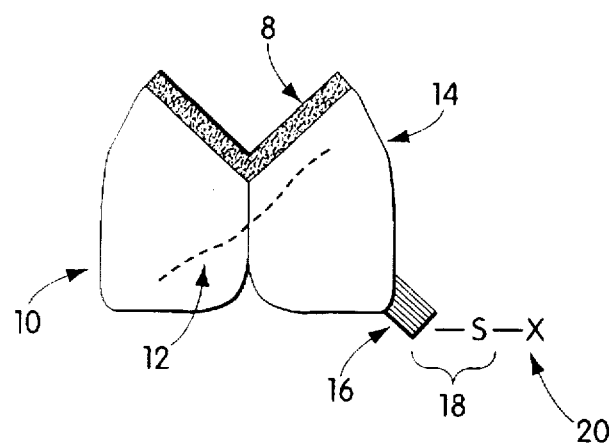
FIG. 2A is a schematic representation of a refolded sFv' protein in its native conformation.
Figure 2B:
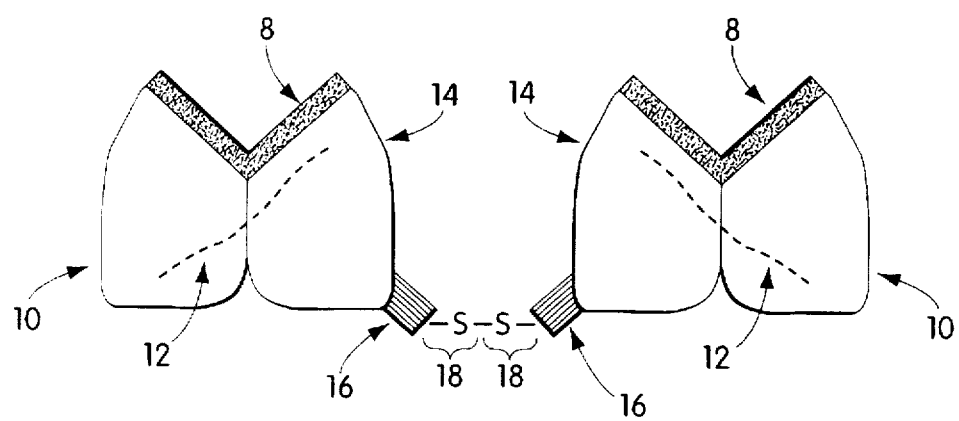
FIG. 2B is a schematic representation showing two folded sFv' polypeptides covalently linked by a disulfide bond.

The sFv' constructs of this invention can be further understood by referring to the accompanying FIGS. 1 and 2. FIG. 1A is a schematic representation of the DNA construct, and FIG. 1B is a schematic representation of the resulting encoded polypeptide chain. FIG. 2 is a schematic representation of the folded sFv' monomer (FIG. 2A) and the dimeric (sFv')$_2$ construct (FIG. 2B). A single-chain Fv (sFv') polypeptide, shown in FIGS. 1 and 2A, comprises: a heavy chain variable region (V$_H$) 10, and a light chain variable region, (V$_L$) 14, wherein the V$_H$ and V$_L$ domains are attached by polypeptide linker 12. The binding domains defined by V$_L$ and V$_H$ include the CDRs 2, 4, 6 and 2', 4', 6', respectively, and FRs 32, 34, 36, 38 and 32', 34', 36', 38', respectively which, as shown in FIG. 2, together define an immunologically reactive binding site or antigenic determinant, 8. Furthermore, the CDRs and FRs may be derived from different immunoglobulins (see infra). The sFv' molecules also contain a C-terminal tail amino acid sequence, 16, comprising an amino acid sequence that will not self-associate with a polypeptide chain having a similar amino acid sequence under physiological conditions, and which contains a means, 18, for the site-directed crosslinking of two such tail sequences. In a currently preferred embodiment, represented in FIGS. 1 and 2, the crosslinking means is the sulfhydryl group of a cysteine amino acid. In the monomeric form of the sFv' the crosslinking means, 18, may be blocked by a blocking group, 20. For instance, the blocking group may be a glutathionyl moiety when the crosslinking means, 18, is a cysteine amino acid.

As will be appreciated by those having ordinary skill in the art, the sequence referred to herein generally as a "C-terminal tail" sequence, peptide bonded to the C-terminus of an sFv and comprising means for crosslinking two sFv polypeptide chains, alternatively may occur at the N-terminus of an sFv ("N-terminal tail") or may comprise part of the polypeptide linker spanning the domains of an individual sFv. The dimeric species created by the crosslinking of sFvs having these alternative "tail" sequences also are contemplated to have a conformation permitting the in vivo binding of a preselected antigen by the binding sites of each of the sFv polypeptide chains. Accordingly, descriptions of how to make and use sFv' monomers and dimers comprising a C-terminal tail sequence are extended hereby to include sFv monomers and dimers wherein the tail sequence having crosslinking means occurs at the N-terminus of an sFv or comprises part of the polypeptide linker sequence.

The CDR and FR polypeptide segments are designed empirically based on sequence analysis of Fv regions of preexisting antibodies, such as those described in U.S. Pat. No. 4,753,894, hereby incorporated by reference. Numerous examples of sFv polypeptide chains now exist in the art and are summarized in Huston et al., 1993, *Intern. Rev. Immunol.* 10: 195–217, hereby incorporated by reference.

The sFv and sFv' polypeptide chains of the invention are biosynthetic in the sense that they are synthesized, transfected into a cellular host, and protein expressed from a nucleic acid containing genetic sequences based in part on synthetic DNA. Synthetic DNA is understood to include recombinant DNA made by ligation of fragments of DNA derived from the genome of a hybridoma, mature B cell clones, a cDNA library derived from natural sources, or by ligation of plural, chemically synthesized oligonucleotides. The proteins of the invention are properly characterized as "antibody binding sites", in that these synthetic single polypeptide chains are able to refold into a 3-dimensional conformation with specificity and affinity for a preselected epitope on an antigen.

A detailed description for engineering and producing sFv proteins by recombinant means appears in U.S. Pat. No. 5,091,513 claiming priority from U.S. Ser. No. 052,800, filed May 21, 1987, assigned to Creative BioMolecules, Inc., hereby incorporated by reference. The polypeptide chains of the invention are antibody-like in that their structure is patterned after regions of native antibodies known to be responsible for antigen recognition.

The single-chain polypeptide chains of the invention are first derived at the DNA level. The sFv DNAs are preferably expressed in *E. coli*, the resulting polypeptide chains being solubilized from inclusion bodies, refolded in vitro, labeled with a detectable moiety, such as $^{99m}$Tc, and dimerized to form a biosynthetic (sFv')$_2$ construct. Of course, the constructs disclosed herein may also be engineered for secretion from the host cell, for example, secretion into the periplasmic space of an *E. coli* cell, as described by Pack and Pluckthun, (*Biochem.*, 1992, 31: 1579–1584), or into the culture supernatant of a mammalian cell (for example, as described by Traunecker, et al., 1991, *EMBO J.* 10: 3655–3659).

The ability to design the single polypeptide chains of the invention depends on the ability to identify Fv binding domains of interest, and to obtain the DNA encoding these variable regions. Hybridoma technology enables the production of cell lines that secrete antibodies to essentially any desired substance that elicits an immune response. For example, U.S. Pat. No. 4,753,894 describes some monoclonal antibodies of interest which recognize c-erbB-2 related antigens on breast cancer cells, and explains how such antibodies were obtained. One monoclonal antibody that is particularly useful in targeting the c-erbB-2 antigen is 741F8 (Bjorn et al., 1985, *Cancer Res.* 45: 1214–1221; U.S. Pat. No. 4,753,894). This antibody specifically recognizes the c-erbB-2 antigen expressed on the surface of various tumor cell lines, and exhibits very little binding to normal tissues. Other monoclonal antibodies that bind c-erbB-2 or related antigens include 520C9 and 454C11 (Frankel et al., 1985, *J. Biol. Resp. Modif.* 4: 273–286; Ring et al., 1989, *Cancer Res.* 49: 3070–3080, Ring et al., 1991, *Molec. Immunol.* 28: 915–917; U.S. Pat. Nos. 4,753,894 and 5,169,774). sFv' sequences with the desired specificity can also be derived from phage antibody cloning of combinatorial V gene libraries. Such sequences could be based on cDNA derived from mice preimmunized with tumor cell membranes bearing c-erbB-2 or related antigenic fragments, (See, for example, Clackson et al, (1991) *Nature* 352: 624–628).

The process of designing DNA encoding the single polypeptide chain of interest can be accomplished as follows. Either synthetic DNA duplexes can be ligated together to form a synthetic gene or relevant DNA fragments can be cloned from libraries. In the latter procedure, mRNA encoding the light and heavy chains of the desired immunoglobulin may be isolated from hybridomas producing the immunoglobulin and reverse transcribed into cDNA. The V$_H$ and V$_L$ genes subsequently can be isolated by standard procedures, for instance, by colony hybridization of cDNA libraries (see for example, Sambrook et al., eds., 1989, *Molecular Cloning*, Cold Spring Harbor Laboratories Press, NY) or by polymerase chain reaction (PCR) (see for example, Innis et al., eds., 1990, *PCR Protocols, A guide to methods and applications*, Academic Press). Both procedures are well known in the art.

Still another approach involves the design and construction of synthetic variable domain genes encoding a predetermined, specific Fv binding site. For example, with the help of a computer program, such as Compugene, one may design and directly synthesize native or near-native FR sequences from a first antibody molecule, and CDR sequences from a second antibody molecule. The resulting $V_H$ and $V_L$ gene sequences can then be genetically linked together by means of a linker connecting the C-terminus of one chain with the N-terminus of the other.

Practice of the invention enables the design and synthesis of various single-chain binding proteins, all of which are characterized by a region having affinity for a preselected epitope on an antigen. Other regions of the biosynthetic protein are designed with the particular planned utility of the protein in mind. Thus, if the reagent is designed for intravascular use in mammals, the FRs may include amino acid sequences which are similar or identical to at least a portion of the FR amino acid sequences of antibodies native to that species. The amino acid sequences constituting the CDRs may be analogous to the sequences from a second, different preexisting antibody having specificity for the antigen of interest (e.g. a murine or other human IgG). Alternatively, the CDRs and FRs may be copied in their entirety from a single pre-existing monoclonal antibody cell line or a desirable sFv species may be cloned from a repertoire library derived from preimmunized or naive animals.

It is noted however, that the linear arrangement of the $V_L$ and $V_H$ domains in the DNA sequence of FIG. 1 is not critical. That is, although the sequence represented in FIG. 1A encodes a heavy chain variable region followed by the light chain variable region, as will be appreciated by those skilled in the art, the sFv may be constructed so that the light and heavy chain domains are in reverse order.

As mentioned above, the $V_H$ and $V_L$ domains of the sFv are linked in the gene construct by means of a linker 12 (FIG. 1A). The linker should be at least long enough (e.g., about 10 to 15 amino acids or at least 40 Angstroms in length) to permit domains 10 and 14 to assume their proper conformations and interdomain relationships. The linkers preferably comprise hydrophilic amino acids that assume an unstructured configuration under physiological conditions, and are free of residues having large side groups that could interfere with proper folding of the $V_H$, $V_L$, or pendant chains. Examples of currently preferred linkers include either part or all of the amino acid sequences $((Gly)_4Ser)_3$ and $((Ser)_4Gly)_3$, set forth in the Sequence Listing as SEQ. ID. NOS.: 7 and 8, respectively. The linker may also include an amino acid sequence homologous to a sequence identified as "self" by the species into which it will be introduced, particularly if a therapeutic application is intended.

Considerations for Suitable C-terminal Tail Sequences

As mentioned above, the sFv' polypeptide chains further comprise a C-terminal tail containing at least one amino acid that can be derivatized or post-translationally modified to enable crosslinking of two such sFv' monomers. In preferred aspects of the invention, the tail sequences include one or more of the sequences Ser-Cys, $(Gly)_4$-Cys and $(His)_6$-$(Gly)_4$-Cys, set forth in the Sequence Listing as SEQ. ID. NOS.: 9, 10, and 11, respectively. The C-terminal tails preferably do not form a-helical structures which self-associate under physiological conditions, such as the α-helical leucine zipper motifs found in DNA binding proteins (O'Shea et al., 1989, *Science* 243: 538–542, O'Shea et al., 1991, *Science* 254: 539–544) or the four-helix bundle motifs found in recombinant ion channels (Hill et al., 1990, *Science* 294: 543–546).

Suitable derivatizable amino acid side chains may be selected from the group consisting of cysteine, lysine, arginine, histidine, glutamate, aspartate and derivatives or modified forms thereof. In a preferred aspect of the invention, cysteine amino acids are incorporated into the C-terminal tail sequences as the crosslinking means.

Also envisioned to be useful are posttranslationally modified amino acids that can be crosslinked in vitro. More specifically, the glycosyl moieties present on glycosylated amino acids, following secretion out of the cell, can be covalently attached in vitro using bifuntional linkers on standard sugar chemistry (see for example, E. A. Davidson (1967) Carbohydrate Chemistry, Holt, Kinehart and Winston, N.Y.; W. J. Lennarz (1980) The Biochemsitry of Glycoproteins and Proteoglycans, Plenum Press, N.Y.). Particularly useful glycosylation sites include the sequences Asn-Xaa-Thr and Asn-Xaa-Ser, wherein Xaa is any amino acid. Where crosslinking of glycosyl moieties is contemplated, the glycosylation sequences need not include a cysteine.

The tail also may comprise an amino acid sequence defining an ion chelation motif which can be used as part of a purification protocol for isolating of the sFv' monomers by metal ion affinity chromatography (e.g., by means of a $(His)_6$ tail on an IMAC chromatography column), as well as for chelating ions of detectable moieties such as Technetium⁻99M or $^{111}$Indium for in vivo imaging applications.

sFv' Coupler Considerations

In the present invention, two monomeric sFv' proteins are crosslinked together through their C-terminal tails to form an $(sFv')_2$ dimer. The term "sFv coupler", as used herein, refers to chemical bridges that join the crosslinking residues in each of the sFv' molecules.

In one preferred aspect of the invention, where the crosslinking residue is a cysteine residue, the chemical bridge can be a disulfide bond. Alternatively, sulfhydryl-specific crosslinking reagents can be used to join two sFv' molecules together. An example of such a cysteine-specific chemical bridge includes the bifunctional crosslinking reagent bismaleimidohexane (BMH), a water insoluble linker that can be obtained from Pierce, Rockford, Ill. Other bifunctional crosslinking agents include heterobifunctional crosslinkers which can be used to join two sFv' species together where the crosslinking residues in each of the sFv' C-terminal tail sequences are different, such as, a C-terminal cysteine on one sFv' and a C-terminal lysine on the other. Useful heterobifunctional crosslinking agents include 4-succinimidyloxycarbonyl-methyl-(2-pyridyldithio)-toluene (SMPT) or N-succinimidyl-3-(2-pyridyldithio) propionate (SPDP), both of which can be obtained from Pierce, Rockland, Ill.

sFv couplers of variable length also can be prepared to limit steric interaction of two coupled sFv' proteins. An example of such an sFv coupler includes a peptide bridge, such as the water soluble bismaleimidocaproyl amino acid (MCA) linker. Although in a preferred aspect of the invention, an MCA-GlySer₃Gly₂Ser₃Lys-MCA linker is used, in theory, any amino acid sequence can be introduced into this type of chemical bridge-spacer group.

Suitable MCA-peptide chemical bridges can be synthesized on polystyrene resins functionalized with hydroxymethylphenoxyacetic acid (HMP) to allow formation of free acids at the C-terminus following deblocking. During the synthesis of the preferred peptide sequence Gly-Ser₃-Gly₂-Ser₃-Lys the C-terminal lysine is esterified to the resin and other amino acids are added as N-α-Fmoc protected derivatives. DIC/ hydroxybenzotriazol activated amino acids are coupled for 90 minutes after which the N-α-Fmoc protected groups are deprotected with 20% piperidine in dimethylformamide (DMF). Upon completion of the synthesis, the peptide is cleaved from the resin and deprotected with 95% trifluoroacetic acid (TFA) in water. The crude peptide then is dissolved in 0.1M phosphate buffer pH 7 and reacted overnight at room temperature with maleimidocaproic acid N-hydroxy-succinimide ester. The resulting homobifunctional peptide crosslinker can be purified by reverse-phase HPLC, for example, on a Vydac 1×25 cm column using acetonitrile/water/TFA buffers.

With this procedure, it is possible to generate linkers having specific lengths and flexibilities. Since polypeptides having particular secondary structures and flexibilities are well documented in the art, it is possible to judiciously design the peptide couplers with optimal length and flexibility to optimize binding to two preselected antigens on a cell surface. As will be appreciated by those skilled in the art, the separation distance between, and interaction of, the sFv' monomers in a dimeric construct of the invention also can be modulated by the judicious choice of amino acids in the tail sequences themselves.

Dimer Considerations

Using the approaches described above, (sFv')$_2$ dimers readily can be prepared wherein the resulting dimers either can be homodimeric, where the CDR sequences define the same epitope binding site, or heterodimeric, where the CDR sequences of each sFv' monomer define different epitope binding sites.

The dimeric constructs of this invention preferably target a pharmacologically active drug (or other ancillary protein) to a site of interest utilizing the bivalent capability of the dimer. Examples of pharmacolcogically active drugs include molecules that inhibit cell proliferation and cytotoxic agents that kill cells. Other, useful molecules include toxins, for instance, the toxic portion of the Pseudomonas exotoxin, phytolaccin, ricin, ricin A chain, or diptheria toxin, or other related proteins known as ricin A chain-like ribosomal inhibiting proteins, i.e., proteins capable of inhibiting protein synthesis at the level of the ribosome, such as pokeweed antiviral protein, gelonin, and barley ribosomal protein inhibitor.

In such cases, one sFv' can be immunologically reactive with a binding site on an antigen at the site of interest, and the second sFv' in the dimer can be immunologically reactive with a binding site on the drug to be targeted. For example, the (sFv')$_2$ dimers may have specificity for both c-erbB-2 and a pharmacologically active drug or cytotoxic agent. The resulting dimer can thus target the agent or drug to tissues expressing the c-erbB-2 antigen in vivo. Alternatively, the construct may bind one or more antigens at the the site of interest and the drug to be targeted is otherwise associated with the dimer, for example, by crosslinking to the chemical bridge itself.

Other bispecific (sFv')$_2$ constructs having particular utility in targeting malignant cells, include constructs wherein one has specificity for a c-erbB-2 or related tumor antigen, and the second determinant has specificity for a different cell surface protein, such as the CD3 antigen found on cytotoxic T-lymphocytes. The heterodimeric (sFv')$_2$ construct then could mediate antibody dependent cellular cytotoxicity (ADCC) or cytotoxic T-lymphocyte-induced lysis of the tumor cells expressing the c-erbB-2 antigen.

Still another bispecific dimeric construct having cytotoxic properties is a bispecific construct with one sFv' capable of targeting a tumor cell and the second being a catalytic sFv' that binds an inactive drug, and subsequently converts it into an active compound (see for example, U.S. Pat. No. 5,219,732). Such a construct would be capable of inducing the formation of a toxic substance in situ. For example, a catalytic sFv' molecule having β-lactamase-like activity can be designed to bind and catalyze the conversion of an inactive lactam derivative of doxorubicin into the active, cytotoxic form. Here the bispecific dimer, having binding affinities for both the preselected antigen and the cytotoxic-lactam derivative, is administered to an individual and allowed to accumulate at the desired location. The inactive, nontoxic cytotoxin-lactam derivative then is administered to the individual. When the derivative is complexed with the bispecific (sFv')$_2$ heterodimer in situ the active form of the drug is released, enhancing both the cytotoxicity and specificity of the drug.

Hybrid sFv' Considerations

In a preferred aspect of the invention a humanized single-chain Fv is envisioned whereby the recombinant sFv' contains CDRs of the murine 741F8 antibody interposed between human FR sequences to generate a humanized c-erbB-2 binding protein. The humanized Fv would be capable of binding c-erbB-2 while eliciting little or no immune response when administered to a patient. A nucleic acid sequence encoding a humanized sFv may be designed and constructed as follows.

FR regions identified by homology searches of the GenBank database can be introduced into an sFv of interest by site-directed mutagenesis to reproduce the corresponding human sequence. Alternatively, homologous human $V_H$ and $V_L$ sequences can be derived from a collection of PCR-cloned human V regions, after which the human FR sequences can be ligated with murine CDR regions to create humanized $V_L$ and $V_H$ genes. A humanized sFv hybrid thus can be created, for instance, where the human FR regions of the human myeloma antibody are introduced between the murine CDR sequences of the murine monoclonal antibody 741F8. The resulting sFv, containing the sequences FR1-CDR1-FR2-CDR2-FR3-CDR3-FR4, contains a murine binding site in a human framework.

By directly sequencing the DNA or RNA in a hybridoma secreting an antibody to a preselected antigen, or by obtaining the sequence from the literature, one skilled in the art can essentially produce any desired CDR and FR sequence. Expressed sequences subsequently may be tested for binding and empirically refined by exchanging selected amino acids in relatively conserved regions, based on observations of trends of amino acid sequences in data bases and/or by using computer-assisted modeling techniques. Significant flexibility in $V_H$ and $V_L$ design is possible because alterations in amino acid sequences may be made at the DNA level.

Of course, the processes for manipulating, amplifying, and recombining DNAs that encode amino acid sequences of interest are generally well known in the art (see, for example, Sambrook et al., 1989, *Molecular Cloning A Laboratory Manual*, 2nd ed. Cold Spring Harbor Press), and therefore, are not described in detail herein. Similarly, methods for identifying the isolated V genes encoding antibody Fv regions of interest are well understood and are described in the patent and other literature.

Expression of Recombinant sFv Proteins

The resulting sFv DNA constructs then are integrated into expression vectors and transfected into appropriate host cells for protein expression. After being translated, the protein may be purified from the cells themselves or recovered from the culture medium.

The expression vectors also may include various sequences to promote correct expression of the recombinant protein. Typical sequences include transcription promoters and termination sequences, enhancer sequences, preferred ribosome binding site sequences, preferred mRNA leader sequences, preferred protein processing sequences, preferred signal sequences for protein secretion, and the like. The DNA sequence encoding the gene of interest also may be manipulated to remove potentially inhibiting sequences or to minimize unwanted secondary structure formation. The resulting synthetic genes can be expressed in appropriate prokaryotic hosts such as various strains of $E.$ $coli$, or in eucaryotic hosts such as Chinese hamster ovary cells (CHO), mouse myeloma, hybridoma, transfectoma, and human myeloma cells. The currently preferred expression system for the present invention is $E.$ $coli$, as disclosed herein.

When the gene is to be expressed in $E.$ $coli$, it is cloned into an expression vector downstream of a strong promoter sequence, such as Trp or Tac, and optionally also may include a gene coding for a leader polypeptide, such as the fragment B (FB) of staphylococcal protein A. The resulting fusion protein, when expressed, accumulates in retractile bodies (also known as inclusion bodies) in the cytoplasm, and may be harvested after disruption of the cells by French press or sonication. The proteins then are solubilized, and refolded in vitro, as described herein. Where the construct is engineered as a fusion protein, the protein is solubilized and the leader sequence preferably cleaved before renaturation. The cleavage site for the leader sequence preferably is immediately adjacent to the sFv polypeptide chain and includes one amino acid or a sequence of amino acids exclusive of any one amino acid or amino acid sequence found in the amino acid structure of the single polypeptide chain.

The cleavage site preferably is designed for specific cleavage by a selected agent. Endopeptidases are preferred, although non-enzymatic (e.g., chemical) cleavage agents may be used. Many useful cleavage agents, for instance, cyanogen bromide (CNBr), dilute acid, trypsin, Staphylococcus aureus V-8 protease, post-proline cleaving enzyme, blood coagulation Factor Xa, enterokinase, and renin, recognize and preferentially or exclusively cleave at particular cleavage sites. One currently preferred peptide sequence cleavage agent is V-8 protease. The currently preferred cleavage site is at a Glu residue. Other useful enzymes recognize multiple residues as a cleavage site, e.g., factor Xa (Ile-Glu-Gly-Arg) or enterokinase (Asp-Asp-Asp-Asp-Lys). Dilute acid preferentially cleaves the peptide bond between Asp-Pro residues, and CNBr in acid cleaves after Met, unless it is followed by Tyr.

Alternatively, the engineered gene may be incorporated into a vector without a sequence encoding a leader polypeptide, and the engineered gene expressed to produce a polypeptide chain that is secreted into the $E.$ $coli$ periplasmic space. The secreted protein then can be isolated and, optionally, purified further using standard methodologies. (See, for example, Pack et al. (1992) $Biochem$ 31:1579–1584.)

If the engineered gene is to be expressed in eucaryotic hybridoma cells, the conventional expression host for immunoglobulins, the gene preferably is inserted into an expression vector containing, for example, the immunoglobulin promoter, a secretion signal, and immunoglobulin enhancers. This plasmid also may contain sequences encoding other polypeptide chains, including part or all of a toxin, enzyme, cytokine, or hormone. The gene then is transfected into myeloma cells via established electroporation or protoplast fusion methods. The transfected cells then may express $V_H$-linker-$V_L$-tail or $V_L$-linker-$V_H$-tail single-chain Fv' polypeptide chains.

The sFv polypeptide chains can be expressed as either inactive or active polypeptide chains. Spontaneously refolded sFv polypeptide chains can be obtained from either prokaryotic or eukaryotic expression systems when the polypeptide chains are secreted for instance, either into the $E.$ $coli$ periplasmic space or the mammalian cell culture medium. These spontaneously refolded polypeptide chains readily can be purified by affinity chromatography. Where the sFv polypeptide chains are obtained in an unfolded, inactive sFv form, for instance, when overexpression of the sFv polypeptide chain in $E.$ $coli$ results in the formation of inclusion bodies, the proteins can be refolded in vitro. Briefly, inclusion bodies are harvested by centrifugation, the sFv, solubilized with denaturants such as guanidine hydrochloride (GuHCl) or urea, and then refolded by dilution of the denaturant under appropriate redox (reduction/oxidation) conditions (see below). The refolded sFv polypeptide chains then can be purified by affinity chromatography. Details for the isolation of inclusion bodies, solubilization and renaturation of the sFv polypeptide chains are well known in the art (see for example. U.S. Pat. No. 5,091,513 and Huston et al., 1988, supra).

Dimerization and Purification of the sFv Polypeptides

The sFv' monomers of the present invention can be dimerized in vivo or in vitro. In the in vivo approach, two sFv' genes can be cotransfected into the host cell wherein the coexpressed sFv' polypeptide chains spontaneously dimerize. Alternatively, the refolded, secreted sFv' polypeptide chain monomers can be isolated from two expression hosts and subsequently dimerized in vitro.

In a preferred aspect of the invention, the sFv' polypeptide chains comprising a single cysteine C-terminal tail residue are expressed in $E.$ $coli$ and form inclusion bodies. The resulting sFv' polypeptide chains are solubilized with denaturants and renatured in vitro, either in the presence or absence of exogenously added glutathione. Surprisingly, the additional C-terminal cysteine residues apparently do not interfere with the refolding process. In some cases however, sFv and sFv' constructs may refold poorly in vitro. These constructs can be "preoxidized prior" to refolding as taught in Huston et al., (1991) $Meth.$ $Enzymol.$ 203:46–88, or, alternatively, the polypeptide chains can be secreted across a membrane bilayer. The latter process spontaneously separates the extra C-terminal cysteine residue from the cysteine residues normally found in the Fv domain, minimizing inappropriate disulfide bond formation. Secretion is the preferred method if the sFv' constructs refold poorly in vitro.

Following renaturation of the sFv' monomers, (sFv')$_2$ dimers readily can be prepared in vitro by air oxidation if cysteine amino acids are present in the C-terminal tail sequences. Alternatively, sulfhydryl specific crosslinking reagents, for instance, the BMH crosslinker or the MCA-peptide-MCA bridge may be used to covalently couple two sFv' chains. The resultant homo or heterodimers, then can be purified by standard size exclusion chromatography. However, when (sFv)$_2$ heterodimers are required, then a preferred purification protocol uses a sequential two step affinity chromatography procedure. Briefly, the heterodimer is exposed to a first chromatographic system having an epitope that interacts specifically with one sFv of the heterodimer. The eluant containing the heterodimer is then exposed to a second system having an epitope that interacts specifically with the other sFv. For specific details of the dimerization and purification procedures, see Example 2.

Considerations for In Vivo Administration

The dimeric constructs may be administered either by intravenous or intramuscular injection. Effective dosages for the single-chain Fv constructs in antitumor therapies or in effective tumor imaging can be determined by routine experimentation, keeping in mind the objective of the treatment.

The pharmaceutical forms suitable for injection include sterile aqueous solutions or dispersions. In all cases, the form must be sterile and must be fluid so as to be easily administered by syringe. It must be stable under the conditions of manufacture and storage, and must be preserved against the contaminating action of microorganisms. This may, for example, be achieved by filtration through a sterile 0.22 micron filter and/or lyophilization followed by sterilization with a gamma ray source.

Sterile injectable solutions are prepared by incorporating the desirable amount of the constructs, disclosed herein, into an appropriate solvent, such as sodium phosphate-buffered saline (PBS), followed by filter sterilization. As used herein, "a physiologically acceptable carrier" includes any and all solvents, dispersion media, antibacterial and antifungal agents that are non-toxic to humans, and the like. The use of such media and agents as pharmaceutically active substances are well known in the art. The media or agent must be compatible with maintenance of proper conformation of the single-chain Fv polypeptide chains, and its use in the therapeutic compositions. Supplementary active ingredients can also be incorporated into the compositions.

A preferred remotely detectable moiety for in vivo imaging includes the radioactive atom Technetium$^{-99m}$ ($^{99m}$Tc), a gamma emitter with a half-life of about 6 hours. Non-radioactive moieties also useful in imaging include nitroxide spin labels as well as lanthanide and transition metal ions all of which induce proton relaxation in situ. In addition to immunoimaging, the complexed radioactive moieties may be used in standard radioimmunotherapy protocols to destroy the targeted cell. Preferred nucleotides for high dose radioimmunotherapy include the radioactive atoms $^{90}$Yttrium ($^{90}$Yt), $^{131}$Iodine ($^{131}$I) and $^{111}$Indium (111 In).

Either the single polypeptide chain sFv' itself, or the spacer groups for linking the sFv' constructs can be labeled with radioisotopes such as $^{131}$I, $^{111}$In and $^{99m}$Tc. $^{99m}$Tc and $^{111}$In are preferred because they can be detected with gamma cameras and have favorable half-lives for in vivo imaging applications. The single polypeptide chains can be labeled, for example, with radioactive atoms such as $^{90}$Ty, $^{99M}$Tc or $^{111}$I via a conjugated metal chelator (see, e.g., Khaw et al., 1980, Science 209: 295; U.S. Pat. No. 4,472,509; U.S. Pat. No. 4,479,930), or by other standard means of linking isotopes to proteins, known to those with skill in the art (see for example, Thankur et al., 1991, *J. Immunol. Methods* 237: 217—224).

The invention is illustrated by the following Examples, which are not intended to be limiting in any way.

EXAMPLES

Example 1. Synthesis and Expression of the sFv Constructs (741F8, 26-10 and 520C9)

The construction of several sFv genes using different but standard recombinant DNA technology, well known to those having ordinary skill in the art, is described below. These procedures include the amplification of the $V_H$ and $V_L$ gene sequences by PCR, the ligation of appropriate synthetic DNA duplexes and the cloning of $V_H$ or $V_L$ genes by colony hybridization.

A. 741F8 sFv'.

The $V_H$ and $V_L$ genes of the 741F8 anti-c-erbB-2 monoclonal antibody were isolated from the cDNA of the parental 741F8 hybridoma line by PCR using primers homologous to the N-terminal coding regions of $V_H$, $V_L$, $C_H1$, and $C_L$. The PCR-amplified $V_H$ and $V_L$ genes were isolated by polyacrylamide gel electrophoresis and cloned into a pUC cloning vector. The first FR region of the 741F8 $V_H$ gene however contained spurious mutations due to the PCR procedure. Errors were rectified by the replacement of the first 70 nucleotides of 741F8 $V_H$ with a similar sequence from 520C9 $V_H$, another c-erbB-2 specific monoclonal antibody.

Restriction sites then were introduced into the ends of the heavy and light chain variable gene segments by site-directed mutagenesis (Kunkel et al., 1985, *Proc. Natl. Acad. Sci. USA* 82: 488–492). A Nco I site encoding methionine was positioned at the N-terminus of $V_H$ for expression in *E. coli*. A Sac I site was created at the 3' end of $V_H$ gene. A Xho I site, together with an adjacent Eco RV site, were created at the N-terminus of $V_L$. A stop codon and a Pst I site were placed at the C-terminal end of $V_L$.

The single-chain Fv gene was constructed by connecting the $V_H$ and $V_L$ genes together with a DNA sequence encoding the 14 residue polypeptide linker, (Ser$_4$Gly)$_2$Ser$_4$, as set forth as amino acids 122 through 135 in the Sequence Listing as SEQ. ID. NOS.: 1 and 2.

A synthetic DNA duplex encoding the C-terminal amino acid sequence, (Gly)$_4$-Cys was inserted into a Hpa I site located near the stop codon at the 3' end of the 741F8 sFv gene. The resulting 741F8 anti-c-erbB-2 sFv' gene was excised from the pUC cloning vector, with the restriction enzymes Nco I and Bam HI (a Bam HI site is located 3' to the C-terminal Pst I site), and inserted into the same sites of a commercial T7 expression vector pET-3d (In-vitrogen, Inc.). The resulting gene, set forth in the Sequence Listing as SEQ. ID. NOS.: 1 and 2, was transformed into *E. coli* BL21-DE (In-vitrogen, Inc.). Protein expression was induced by the addition of IPTG to the culture medium.

B. 26-10 sFv'

Construction of the anti-digoxin 26-10 sFv has been described previously (Huston et al., 1988, *Proc. Natl. Acad. Sci. USA* 85; 5879–5883, and U.S. Pat. No. 5,091,513, both of which are hereby incorporated by reference). Briefly, the synthetic gene was constructed by ligating multiple synthetic DNA duplexes together. The C-terminal DNA duplex coding for the amino acid sequence (Gly)$_4$-Cys subsequently was ligated into a Hpa I restriction site close to the 3' end of the 26-10 sFv gene. The resulting sFv' gene, set forth in the Sequence Listing as SEQ. ID. NOS.: 3 and 4, was then inserted into the *E. coli* expression vector pET-3d. This plasmid was subsequently transformed into *E. coli* BL21-DE (In-vitrogen, Inc.) and protein expression induced by the addition of IPTG to the culture medium.

C. 520C9 sFv.

The 520C9 sFv was generated by linking together the $V_H$ and $V_L$ genes, cloned from a 520C9 hybridoma cDNA library, with a serine rich linker. Briefly, the $V_H$ and $V_L$ genes were cloned from the 520C9 hybridoma cDNA library using probes directed toward the antibody constant (C) and joining (J) regions. Appropriate restriction sites were introduced at the ends of each gene by site-directed mutagenesis (Kunkel et al., 1985, *Proc. Natl. Acad. Sci. USA* 82:

488–492). The $V_H$ and $V_L$ genes were then ligated together with a serine rich linker. The resulting 520C9 sFv gene, set forth in the Sequence Listing as SEQ. ID. NOS.: 5 and 6, was transformed into the *E. coli* expression vector and expressed as described above and in co-pending U.S. Ser. No. 831,967, incorporated therein by reference.

EXAMPLE 2. Renaturation, Dimerization and Purification of sFv Proteins

A. Renaturation and Purification of sFv monomers.

Protocols for renaturing sFv monomers derived from *E. coli* inclusion bodies are described below. In separate experiments the 7418, 26-10 and 520C9 sFv polypeptides were expressed in *E. coli*. The unfolded sFv proteins were solubilized from inclusion bodies and refolded under appropriate redox conditions. The refolded sFv polypeptide chains were purified by affinity chromatography or by a combination of ion-exchange and size exclusion chromatography when affinity chromatography was not feasible or expedient.

Renaturation of 741F8 sFv'.

Inclusion bodies containing the 741F8 sFv' proteins were washed in a buffer containing 25 mM Tris, 10 mM EDTA, 1.5M GuHCl, pH 8.0 and solubilized in 25 mM Tris, 10 mM EDTA, 7M GuHCl, pH 9.0 to an $OD_{280}$ nm of about 25–50. The sample was reduced overnight at room temperature by the addition of dithiothreitol (DTT) to a final concentration of 10 mM. The thiol groups were converted into mixed disulfides with glutathione by the addition of solid oxidized glutathione to a final concentration of 100 mM. The solution was adjusted to pH 9.0 and incubated for 4 hr at room temperature. The 741F8 sFv' polypeptide chains then were refolded in vitro to generate stable monomers with their C-terminal cysteines remaining blocked with glutathione. The 741F8 sFv' mixed disulfide preparation was diluted to an $OD_{280}$ of about 0.15 by the addition of 10 mM Tris, 4 mM EDTA, 6M urea, pH 8.5 at 4° C. After two hours an equal volume of 10 mM Tris, 4 mM EDTA, 1 mM reduced glutathione, pH 8.5, precooled to 4° C., was added with rapid mixing to reduce the urea concentration to 3M. After dilution, the samples were allowed to renature for 72 hr at 4° C.

Renaturation of 26-10 sFv'.

Inclusion bodies containing the 26-10 sFv' proteins were washed with 25 mM Tris, 10 mM EDTA and solubilized in 6M GuHCl, 25 mM Tris, 10 mM EDTA, pH 8.7 to an $OD_{280}$ nm of about 10 to 20. The dissolved proteins were reduced by overnight incubation at room temperature after the addition of DTT to 10 mM. The reduced protein could also be blocked with oxidized glutathione as noted above for the 741F8 sFv' polypeptide. The reduced, denatured 26-10 sFv' polypeptides were refolded in a manner similar to that for the 741F8 sFv' by diluting the preparation into a buffer containing 3M urea, 0.1 mM oxidized and 0.01 mM reduced glutathione to give a final protein concentration of about 0.15 mg/ml. After overnight incubation at 4° C., the mixture was dialyzed against PBS containing 0.05M $KH_2PO_4$ 0.15M NaCl, pH 7 for two days at 4° C.

Renaturation of 520C9 sFv.

The inclusion bodies containing the 520C9 sFv were washed with 25 mM Tris, 10 mM EDTA, pH 8.0. 1M GuHCl and solubilized in 25 mM Tris, 10 mM EDTA, 6M GuHCl, 10 mM dithiothreitol (DTT), pH 9.0. The material was ethanol precipitated and resuspended in 25 mM Tris, 10 mM EDTA, 6M urea, 10 mM DTT, pH 8.0 and fractionated by ion exchange chromatography to remove contaminating nucleic acids and *E. coli* proteins before renaturation of the sFv. The material that did not bind to a DEAE Sepharose Fast Flow (FF) column was precipitated by lowering the pH to 5.5 with 1M acetic acid. The pellet was resolubilized in 25 mM Tris, 10 mM EDTA, 6M GuHCl, 10 mM DTT, pH 9.0 and oxidized by overnight incubation at room temperature following dilution into a buffer containing 25 mM Tris, 10 mM EDTA 6M GuHCl, 1 mM oxidized glutathione, 0.1 mM reduced glutathione, pH 9.0. After overnight oxidation the sample was dialyzed against 10 mM $NaH_2PO_4$, 1 mM EDTA, 150 mM NaCl, 500 mM urea, pH 8.0 and the sample clarified by filtration through a membrane with a 100 kD mol. wt. cut-off prior to purification on a c-erbB-2 affinity column.

Purification of the refolded sFv Polypeptides.

The refolded 26-10 sFv' polypeptide chains were purified by ouabain-Sepharose affinity chromatography, as described for the 26-10 sFv constructs (Huston, et. al., 1988, *Proc. Natl Acad. Sci. USA* 85; 5879–5883 and Tai, et al., 1990, *Biochem.* 29, 8024–3080, both of which are hereby incorporated by reference). The refolded 520C9 sFv polypeptide chain was similarly purified using a c-erbB-2-agarose affinity column. In this case, the refolded samples were loaded onto a c-erbB-2 affinity column, the column washed with PBS, and the 520C9 sFv polypeptides eluted with PBS pH 6.1 containing 3M LiCl. The buffer was then exchanged by dialysis. The c-erbB-2 affinity column preferably was prepared by linking the extracellular domain of c-erbB-2 onto agarose beads.

Briefly, the c-erbB-2 sequence coding for its extracellular domain (ECD) was derived from the baculovirus expression vector described previously (Ring et al., 1992, *Mol. Immunol.* 28; 915–917). A DNA duplex encoding the $His_6$ peptide was ligated to the 3' end of the ECD gene, and the construct expressed in CHO cells. The ECD polypeptide was purified from the CHO cell culture medium on an IMAC metal affinity column (Pharmacia, Piscataway, N.J.), as described in Skerra, et al., 1991, *Bio/Technology* 9: 273–278, and the eluted ECD proteins attached onto agarose beads to generate the c-erbB-2-agarose affinity resin.

The renatured 741F8 sFv' polypeptides were purified by a combination of ion exchange and size exclusion chromatography. Briefly, the renatured 741F8 sFv' preparation was passed through a DEAE-cellulose column and the 741F8 sFv' in the unbound fraction adjusted to pH 5.0 before loading on an S-Sepharose FF column. The 741F8 sFv' polypeptide chains were eluted with PBS containing 2 mM EDTA and 3M urea, and dialyzed against 10 mM Tris, 2 mM EDTA, 20 mM NaCl, pH 7.5 at 200° C. The precipitate was harvested by centrifugation, dissolved in a suitable buffer, and passed through a Q-Sepharose FF column. The unbound material was adjusted to pH 5.5 and reloaded onto a S-Sepharose FF column. The 741F8 sFv' polypeptides were eluted with a PBS, 2 mM EDTA, 100 mM NaCl, 3M urea buffer and dialyzed against PBS, 2 mM EDTA. The precipitate was harvested again by centrifugation, dissolved in a suitable buffer, sucrose added to 5% (w/v), and the 741F8 sFv' concentrated to 5 mg/ml in a YM10 membrane concentrator (Amicon). The 741F8 sFv' polypeptide chains were fractionated by gel filtration chromatography using a S-200 HR column (Pharmacia LKB Biotechnology) and a PBS, 2 mM EDTA buffer.

B. Dimerization of the sFv' Constructs

Dimerization of sFv' monomers can be induced using standard crosslinking conditions. Where disulfide bond formation is desired, the monovalent sFv' polypeptide chains initially are deblocked by mild reduction and (sFv')$_2$ dimers formed by crosslinking the sFv' polypeptides either by disulfide linkages or by thioether linkages with the BMH or MCA-peptide-MCA crosslinking reagents.

In order to generate disulfide linked constructs the purified 741F8 and 26-10 sFv' preparations were dialyzed against 50 mM Tris, 150 mM NaCl, pH 8.5. The C-terminal glutathionyl blocking groups were removed by the addition DTT to a concentration of 2 mM followed by overnight incubation at room temperature. Excess reducing agent was removed by extensive dialysis against 50 mM Tris, 150 mM NaCl, pH 8.5, during which the majority of the sFv' polypeptides oxidized into the homodimeric form.

In order to generate BMH and MCA-peptide-MCA crosslinked constructs, sFv' polypeptide chains in PBS first were reduced for two hours at room temperature by the addition of DTT to a final concentration of 1 mM. The samples were desalted by gel filtration chromatography using a PBS, 1 mM EDTA buffer. A 4–5 fold molar excess of either the BMH or MCA-peptide-MCA linkers, both dissolved in dimethylsulfoxide, were added to the reduced protein and incubated for at least 12 hours at room temperature. The resulting dimers were then purified by HPLC gel filtration chromatography.

A modification of the procedure of Brennan, et al. (1985, Science 229: 81–83) may be used to generate disulfide linked sFv' heterodimers. For example, in order to link the 741F8 and 26-10 sFv' polypeptides a thionitrobenzoate (TNB) derivative of the 26-10 sFv' (26-10 sFv'-TNB) was mixed with mildly reduced 741F8 sFv'. The 26-10 sFv'-TNB was prepared by reducing the 26-10 sFv' in PBS with 15 mm 2-mercaptoethylamine for 30 minutes at room temperature. The reducing agent was removed by gel filtration and the reduced 26-10 sFv' reacted with 2.2 mM dithionitrobenzoate (DTNB) for 3 hours. The active 26-10 sFv'-TNB was adsorbed onto onto ouabain-Sepharose. The glutathionyl blocked 741F8 sFv' monomer in 25 mM Tris, 150 mM NaCl, pH 8.2 was reduced for 2 hours at room temperature by the addition of DTT to a final concentration of 1 mM. The excess DTT was removed by gel filtration and the reduced 741F8 sFv' reacted overnight at room temperature with the 26-10 sFv'-TNB complexed to ouabain-Sepharose. The progress of the reaction was monitored spectroscopically at 412 nm, the absorbance maximum of the TNB anion.

C. Purification of (sFv')₂ Dimers.

The (sFv')₂ homodimers may be separated from the sFv' monomers by gel filtration chromatography. Following dimerization, the sFv' preparations are dialyzed against PBS containing 1 mM EDTA, 3M urea, 0.03% azide, to disrupt any non-covalent homodimers and fractionated by HPLC on a TSK-G20000SW column using the same buffer. The procedure requires two passes for purification of the (sFv')₂ homodimers to homogeneity. The purified homodimers may be dialyzed either against PBS or any other suitable buffer prior to use.

The (sFv')₂ heterodimers can be separated by a two step affinity chromatography procedure taking advantage of the bivalent nature of the dimer. For instance, during the the purification of the 741F8/26-10 heterodimer the mixture initially was loaded onto an ouabain-Sepharose column, washed with a PBS, 1M NaCl buffer, to remove any non-specifically adsorbed material, and rewashed with PBS to reduce the salt concentration. The reactive 26-10 sFv' species bound to the resin were eluted with 20 mM ouabain in PBS and the eluate dialyzed against PBS to remove the cardiac glycoside. The 741F8/26-10 heterodimers were then repurified on a c-erbB-2-agarose affinity column taking advantage of the ECD binding site in the heterodimer. After the preparation was loaded onto the c-erbB-2 affinity column, it is washed with PBS and the (sFv')₂ heterodimer eluted with 25 mM Tris, 10 mM EDTA, 5M LiCl, pH 6.8. Prior to use, the buffer was exchanged with PBS by dialysis.

EXAMPLE 3. Immunoreactivity of the Monomeric and Dimeric sFv Polypeptides

A. Radiolabeling of the sFv° Constructs.

The sFv' polypeptides may be labeled by the chloramine-T method as described (DeNardo, et al., 1986, Nucl. Med. Biol. 13: 303–310). Briefly, 1.0–2.0 mg of sFv' was combined with $^{125}$I [14–17 mCi/μg] (Amersham, Arlington Heights, Ill.) at an iodine to protein ratio of 1:10 in a 12×75 mm plastic test tube. 10 μl [1 mg/ml] of chloramine-T (Sigma, St. Louis, Mo.) per 100 μg of protein was added and the mixture incubated for three minutes at room temperature. After the reaction was terminated, unincorporated $^{125}$I was separated from the labeled sFv' by the spun-column method of Meares, et al., 1984, Anal. Biochem. 142: 68–78. Specific activities of 0.2–1.0 mCi/mg for the $^{125}$I-labeled products may be routinely obtained.

B. Competition ELISA

In order to prepare c-erbB-2, SK-Br-3 breast cancer cells (Ring et al., 1989, Cancer Res. 49: 30703080), were harvested and resuspended in 10 mM NaCl, 0.5% Nonidet-P40, pH 8. Insoluble debris was removed by centrifugation and the extract filtered through 0.45 Millex HA and 0.2Millex GV filters. 40 μl of the extract was added to each well of a 96 well plate and incubated overnight at 37° C. The plates then were washed with PBS and non-specific binding sites blocked following the addition of PBS containing 1% skim milk by incubation for one hour at room temperature. The sFv and 520C9 Fab samples, diluted in PBS, were added to the wells and incubated for 30 mins at room temperature. A control containing only dilution buffer was also included.

In order to quantitate the reaction, 20 μl of a 520C9-horseradish peroxidase (HRP) probe (Zymed Labs., South San Francisco, Calif.), diluted to 14μl/ml in PBS containing 1% skim milk, was added to each well and incubated for one hour at room temperature. The plate was then washed four times with PBS, the peroxidase substrate added and incubated for 30 minutes at room temperature. The reaction was quenched with $H_2SO_4$ and the $OD_{150\ nm}$ values measured.

Figure 3:
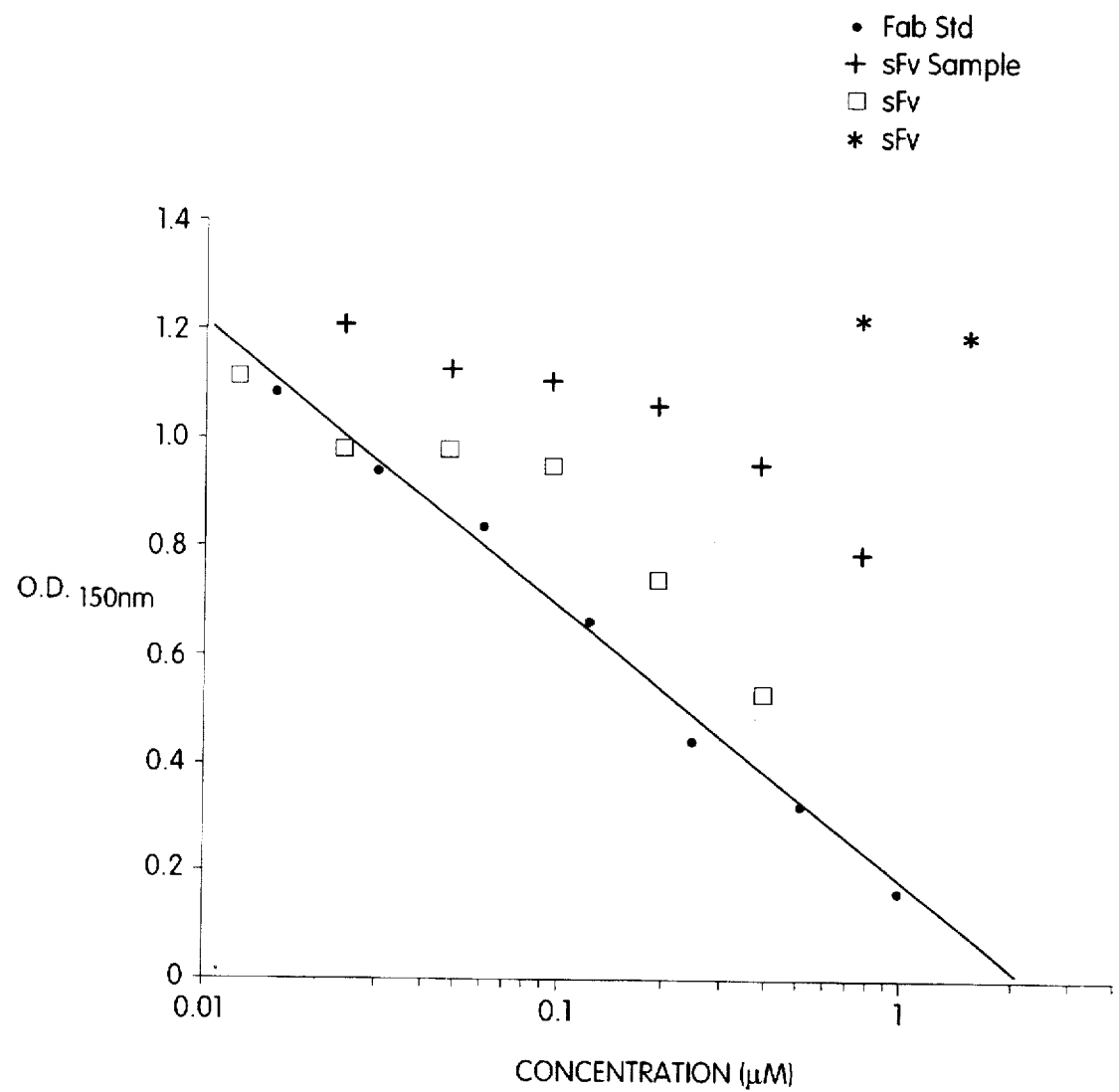
FIG. 3 is a graphic representation of an in vitro competition assay comparing the c-erbB-2 binding activity of an Fab fragment of the 520C9 monoclonal antibody (filled dots), with that of biosynthetic 520C9 sFv at two different stages of purification: mixture of folded and unfolded sFv (+) or affinity-purified sFv (squares), and with a material that did not bind to the affinity column (*)

FIG. 3 compares the binding ability of the parental 520C9 Fab fragment, together with the 520C9 sFv single-chain binding protein. The 520C9 sFv samples included the material obtained following renaturation of the polypeptide in vitro, a sample purified on a c-erbB-2 agarose affinity column, and the material that did not bind to the column. The fully purified 520C9 sFv polypeptide exhibits an affinity for c-erbB-2 indistinguishable from the parent 520C9 Fab fragment.

C. Biodistribution Studies.

In vivo immunotargeting tissue imaging studies were performed using standard procedures. Approximately 2.5× 10⁶ SK-OV-3 cells (a human ovarian cancer cell line that expresses c-erbB-2 on the cell surface) in log phase were implanted subcutaneously onto the hips of four to six week old C.B17/ICI-scid mice. Three days after Lugol's solution was placed in the drinking water to block the accumulation of radioiodine in the thyroid, the mice were used in the biodistribution assays.

The radiolabeled sFv' and Fab preparations were diluted in PBS for these studies. The biodistribution of the glutathionyl-blocked 741F8 sFv' monomers, and the 741F8 and 26-10 (sFv')₂ constructs were compared after identical doses of the radiolabeled protein was administered by injection in each case. The total injected doses were determined by counting each animal on a Series 30 multichannel analyzer/probe system (probe model #2007, Canaberra, Meridian, Conn.). Groups of 3–6 mice were sacrificed twenty four hours after injection, the tumors and organs were removed, weighed and counted in a gamma counter to determine the amount of radiolabel incorporated into the tissues. From these measurements, the percentage of the initial injected dose incorporated per gram of tissue (% ID/gram) or the amount of label incorporated into the tumor relative to the amount of radiolabel incorporated into the other organs (T:O ratio) were determined. For specific details see DeNardo, et al., 1977, *Cancer*, 40: 2923–2929, or Adams, et al., 1992, *Antibody, Immunoconjugates, and Radiopharmaceuticals* 5: 81–95, both of which are hereby incorporated by reference. Specificity indices also can be determined by dividing the T:O ratios of the $^{125}$I-741F8 sFv' by the corresponding T:O ratios of the $^{125}$I-26-10 sFv'. The results of the biodistribution studies 24 hours post administration are summarized in FIGS. 4 and 5. The mean standard error (SEM) for each value is less than 30%, except where indicated.

The disulfide linked 741F8 (sFv')$_2$ homodimers exhibit identical tumor specificities when compared to the monomeric 741F8 sFv' polypeptide chains. The T:O ratios of the 741F8 sFv' constructs consistently exceed those for the 26-10 sFv' constructs, demonstrating the binding specificity of the 741F8 constructs for the tumors (FIG. 4). In addition, the 741F8 (sFv')$_2$ dimers generally exhibit higher T:O ratios relative to that of the monomeric species, particularly for the disulfide bonded sFv' 741F8 (sFv'-(Gly)$_4$Cys)$_2$ and the MCA linked 741F8 (sFv')$_2$ homodimers. In addition, the 741F8 (sFv')$_2$ homodimers localize in greater amounts in the tumors relative to the monomeric sFv' species (FIG. 5).

Figure 6:
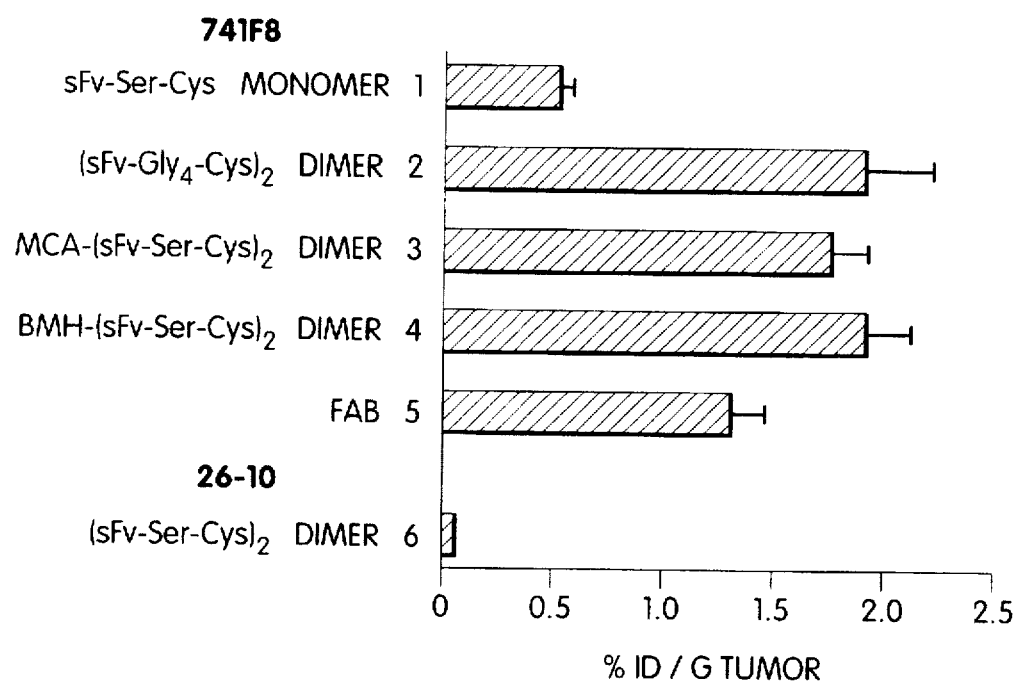
FIG. 6 is a graphic representation summarizing the comparative tumor retention properties of monomeric and dimeric forms of different sFv' constructs and Fabs represented by bars 1–6. The sFv' species represented by bars 1–5 are based on thr V regions of the 741F8 monoclonal antibody. Bar 1 refers to intravenously (i.v.) administered glutathionyl-(sFv'-SerCys) monomer, bar 2 to disulfide linked (sFv'-Gly$_4$-Cys)$_2$, bar 3 to MCA combined (sFv-Ser-Cys)$_2$, bar 4 to BMH cross-linked (sFv-Ser-Cys)$_2$, bar 5 to 741F8 Fab and bar 6 to the 26-10 disulfide linked (sFv-Ser-Cys)$_2$.

In a separate comparative study with $^{125}$I-labeled 26-10 (sFv')$_2$ and the following species of $^{125}$I-labeled 741F8: sFv' monomers, Fab, disulfide linked (sFv'-Gly$_4$Cys)$_2$ homodimers, and MCA- and BMH-linked (sFv')$_2$ homodimers, the in vivo tumor localization properties of these molecules were compared (%ID/gram tumor tissue, see FIG. 6). As is evident from the figure, the tumor localization properties of all of the dimeric 741F8 (sFv')$_2$ constructs are significantly greater than those observed with the 741F8 Fab, the 741F8 sFv' monomer and the 26-10 (sFv')$_2$ dimer (FIG. 6). The results demonstrate that the increased apparent avidity and enhanced in vivo imaging of the (sFv')$_2$ dimer is due, at least in part, to its improved retention in tumor tissue.

EMBODIMENTS

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

---

What is claimed is:

1. A method of imaging a preselected antigen expressed in a mammal, said method comprising the steps of:
   (a) administering to said mammal at a concentration sufficient for extracorporeal detection of a said preselected antigen, a composition comprising a pharmaceutically acceptable carrier in combination with a dimeric biosynthetic construct that binds at least one preselected antigen, wherein the construct comprises
      two separate polypeptide chains, each of which have
         an amino acid sequence defining an sFv comprising two polypeptide domains connected by a polypeptide linker spanning the distance between the C-terminus of one domain and the N-terminus of the other, the amino acid sequence of each said domain comprising complementarity determining regions (CDRs) interposed between framework regions (FRs), the CDRs and FRs of each said sFv together defining a binding site immunologically reactive with a said preselected antigen, and
         a C-terminal tail essentially free of helical character under physiological conditions and comprising at least one amino acid having a derivatizable amino acid side chain, and
      an sFv coupler linking together each said sFv through the derivatizable amino acid side chain disposed within the C-terminal tail of each said sFv, said dimeric biosynthetic construct having a conformation wherein the binding site of each said sFv is operative to bind a said preselected antigen when said dimeric biosynthetic construct is administered to said mammal; and
   (b) detecting said dimeric biosynthetic construct bound to a said preselected antigen.

2. The method of claim 1, wherein said dimeric biosynthetic construct further comprises a detectable moiety.

3. The method of claim 2, wherein said detectable moiety comprises a radioactive atom.

4. The method of claim 3, wherein said detectable moiety comprises Technetium$^{-99m}$.

5. The method of claim 1 for use in magnetic resonance imaging.

6. The method of claim 1, wherein said preselected antigen is c-erbB-2 or a c-erbB-2 related antigen.

7. A method of imaging a preselected antigen expressed in a mammal, said method comprising the steps of:
   (a) administering to said mammal at a concentration sufficient for extracorporeal detection of a said preselected antigen a composition comprising a pharmaceutically acceptable carrier in combination with a dimeric biosynthetic construct that binds at least one preselected antigen wherein the construct comprises
      two separate polypeptide chains, each of which have
         an amino acid sequence defining an sFv comprising two polypeptide domains connected by a polypeptide linker spanning the distance between the C-terminus of one domain and the N-terminus of the other, the amino acid sequence of each said domain comprising complementarity determining regions (CDRs) interposed between framework regions (FRs), the CDRs and FRs of each said sFv together defining a binding site immunologically reactive with a said preselected antigen, and
         an N-terminal tail comprising at least one amino acid having a derivatizable amino acid side chain, and
      an sFv coupler linking together each said sFv through the derivatizable amino acid side chain disposed within the N-terminal tail of each said sFv, said dimeric biosynthetic construct having a conformation wherein the binding site of each said sFv is operative to bind a said preselected antigen when said dimeric biosynthetic construct is administered to said mammal; and
   (b) detecting said dimeric biosynthetic construct bound to a said preselected antigen.

8. The method of claim 7, wherein said dimeric biosynthetic construct further comprises a detectable moiety.

9. The method of claim 8, wherein said detectable moiety comprises a radioactive atom.

10. The method of claim 9, wherein said detectable moiety comprises Technetium$^{-99m}$.

11. The method of claim 7, for use in magnetic resonance imaging.

12. The method of claim 7, wherein said preselected antigen is c-erbB-2 or a c-erbB-2 related antigen.

13. A method of imaging a preselected antigen expressed in a mammal, said method comprising the steps of:
   (a) administering to said mammal at a concentration sufficient for extracorporeal detection of a said preselected antigen, a composition comprising a pharmaceutically acceptable carrier in combination with a dimeric biosynthetic construct that binds at least one preselected antigen, wherein the construct comprises two separate polypeptide chains, which have

- an amino acid sequence defining an sFv comprising two polypeptide domains connected by a polypeptide linker spanning the distance between the C-terminus of one domain and the N-terminus of the other, the amino acid sequence of each said domain comprising complementarity determining regions (CDRs) interposed between framework regions (FRs), the CDRs and FRs of each said sFv together defining a binding site immunologically reactive with a said preselected antigen,
- one of said polypeptide chains further comprising an amino acid sequence defining an N-terminal tail comprising at least one amino acid having a derivatizable amino acid side chain, and
- the other of said polypeptide chains further comprising an amino acid sequence defining a C-terminal tail comprising at least one amino acid having a derivatizable amino acid side chain;
- an sFv coupler linking together each said sFv through the derivatizable amino acid side chain disposed within the N-terminal tail of one polypeptide chain and the derivatizable amino acid side chain disposed within the C-terminal tail of the other polypeptide chain, said dimeric biosynthetic construct having a conformation wherein the binding site of each said sFv is operative to bind a said preselected antigen when said dimeric biosynthetic construct is administered to said mammal; and (b) detecting said dimeric biosynthetic construct bound to a said preselected antigen.

14. The method of claim 13, wherein said dimeric biosynthetic construct further comprises a detectable moiety.

15. The method of claim 14, wherein said detectable moiety comprises a radioactive atom.

16. The method of claim 15, wherein said detectable moiety comprises Technetium$^{-99m}$.

17. The method of claim 13, for use in magnetic resonance imaging.

18. The method of claim 13, wherein said preselected antigen is c-erbB-2 or a c-erbB-2 related antigen.

19. The method of claim 1, wherein said dimeric biosynthetic construct is a homodimer.

20. The method of claim 7, wherein said dimeric biosynthetic construct is a homodimer.

21. The method of claim 13, wherein said dimeric biosynthetic construct is a homodimer.

* * * * *